United States Patent [19]
Milo et al.

[11] Patent Number: 5,429,136
[45] Date of Patent: Jul. 4, 1995

[54] IMAGING ATHERECTOMY APPARATUS

[75] Inventors: Charles Milo, San Mateo; Gerald Hansen, Newark; Fred H. Co, Santa Clara, all of Calif.

[73] Assignee: Devices for Vascular Intervention, Inc., Redwood City, Calif.

[21] Appl. No.: 91,160

[22] Filed: Jul. 13, 1993

Related U.S. Application Data

[63] Continuation-in-part of Ser. No. 51,521, Apr. 21, 1993, abandoned.

[51] Int. Cl.⁶ ............................................. A61B 8/12
[52] U.S. Cl. ........................ 128/660.03; 128/662.06; 606/159
[58] Field of Search ............ 128/660.03, 662.06; 606/159

[56] References Cited

U.S. PATENT DOCUMENTS

| | | | |
|---|---|---|---|
| Re. 33,569 | 4/1991 | Gifford et al. | 606/159 |
| 4,711,774 | 9/1988 | Simpson | 128/305 |
| 4,794,931 | 12/1990 | Yock | 128/660.03 |
| 4,979,951 | 12/1990 | Simpson | 606/159 |
| 5,000,185 | 3/1991 | Yoch | 128/662.06 X |
| 5,024,234 | 6/1991 | Leory et al. | 128/662.06 X |
| 5,041,089 | 8/1991 | Mueller et al. | 604/96 |
| 5,070,879 | 12/1991 | Herres | 128/662.06 X |
| 5,071,425 | 12/1991 | Gifford | 606/159 |
| 5,092,873 | 3/1992 | Simpson | 606/159 |
| 5,135,531 | 8/1992 | Shibes | 606/159 |
| 5,226,847 | 7/1993 | Thomas, III et al. | 128/662.06 |
| 5,250,059 | 10/1993 | Andreas et al. | 606/159 |

*Primary Examiner*—Francis Jaworski
*Attorney, Agent, or Firm*—Douglas A. Chaikin; Hopkins & Carley

[57] ABSTRACT

An atherectomy catheter having ultrasound imaging capability provided by an acoustic transducer disposed within a catheter housing which includes a circular cutting edge for removal of stenotic tissue. Risk of induced emboli is reduced by arrangements of transducer and cutter maneuvering members which permit the cutting edge to remain shielded by the housing during catheter positioning and scanning. Both single and array transducers are employed in a variety of configurations.

36 Claims, 9 Drawing Sheets

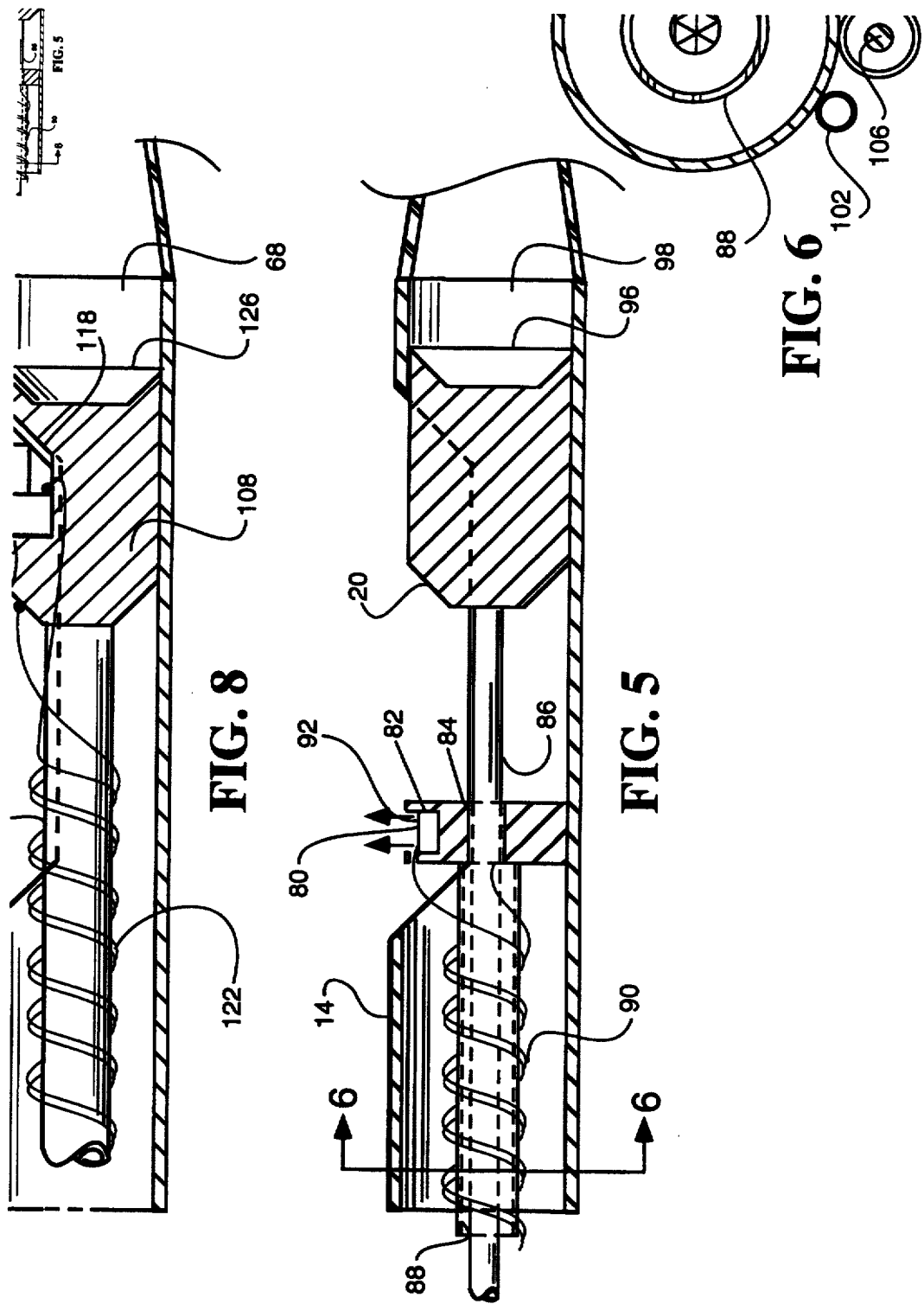

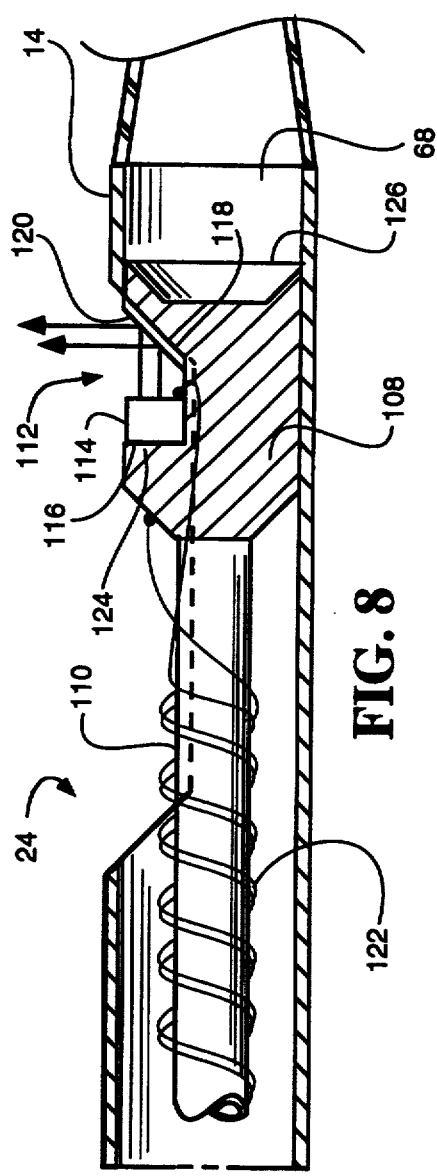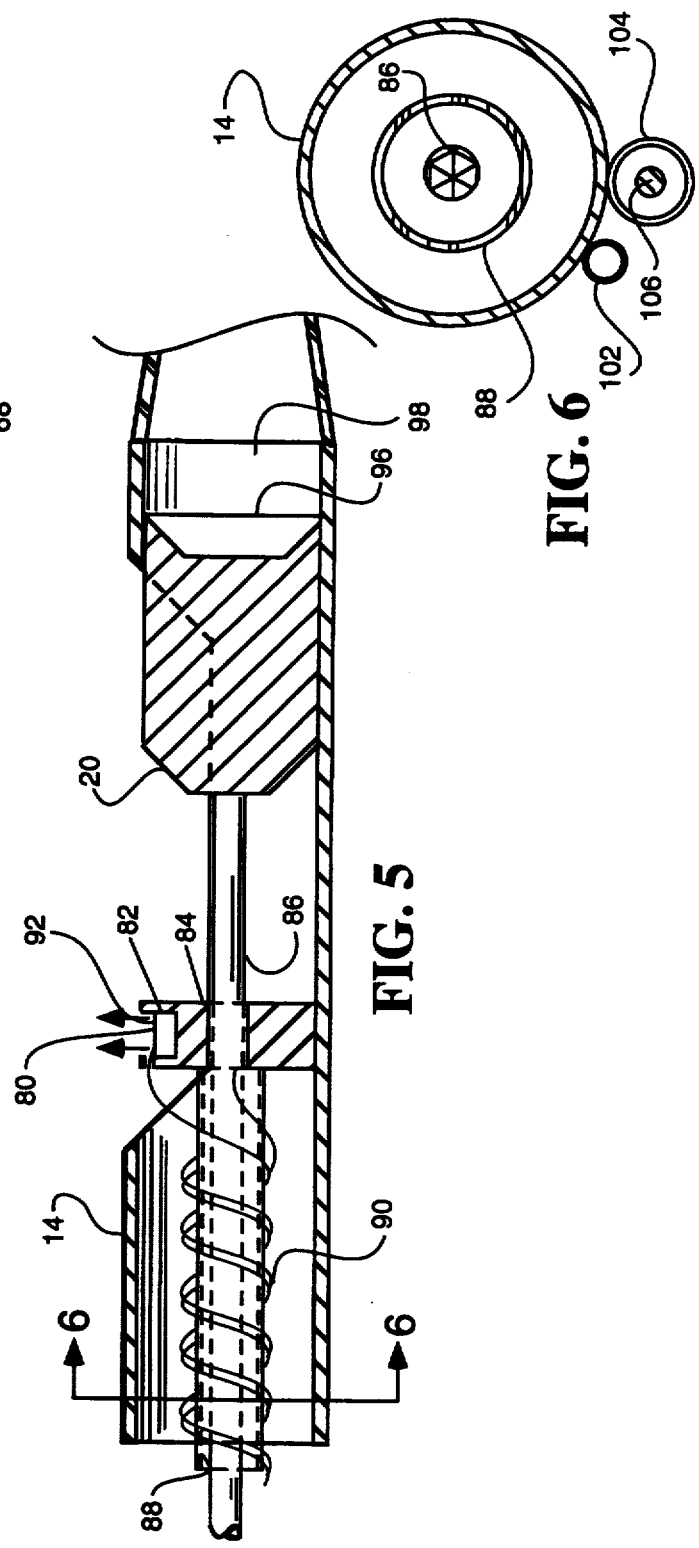

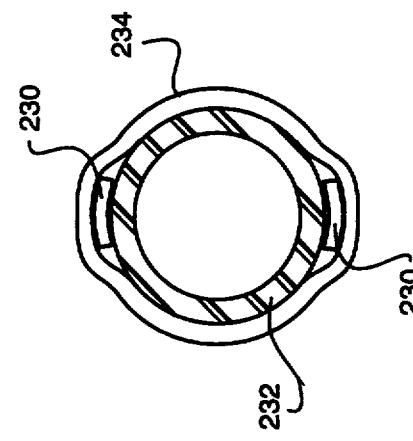
FIG. 17
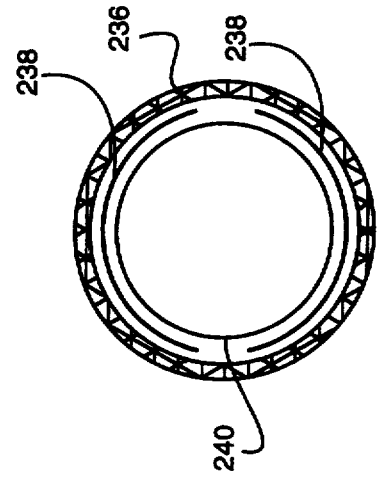
FIG. 18
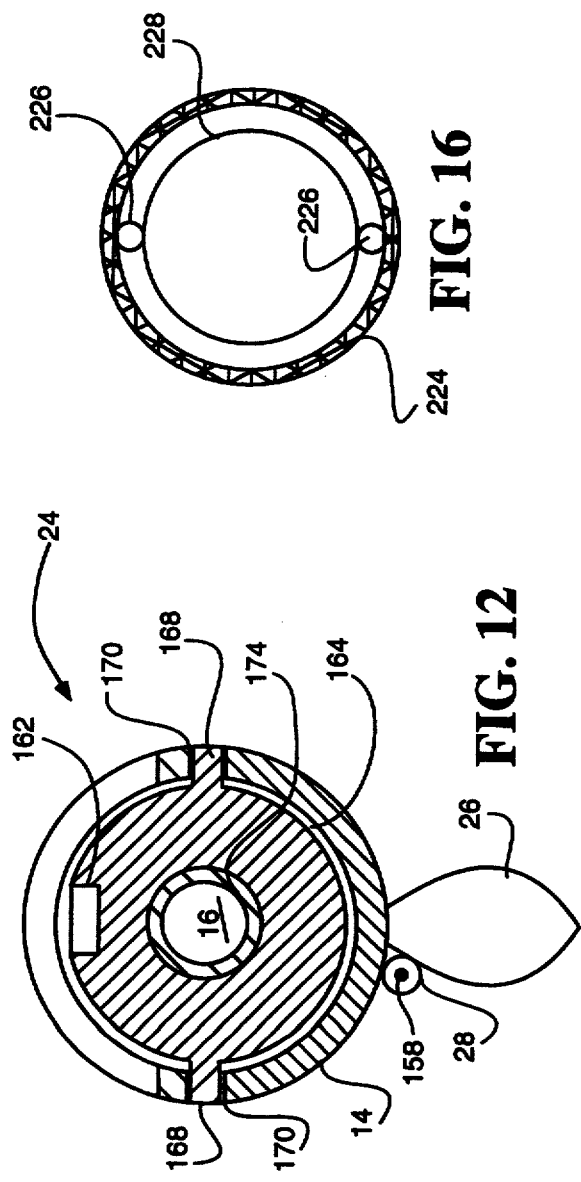
FIG. 16
FIG. 12
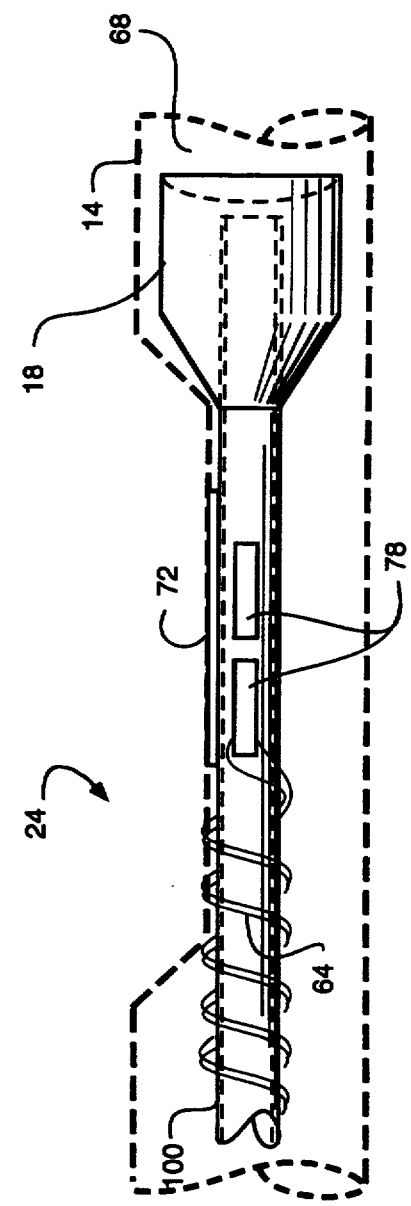
FIG. 7

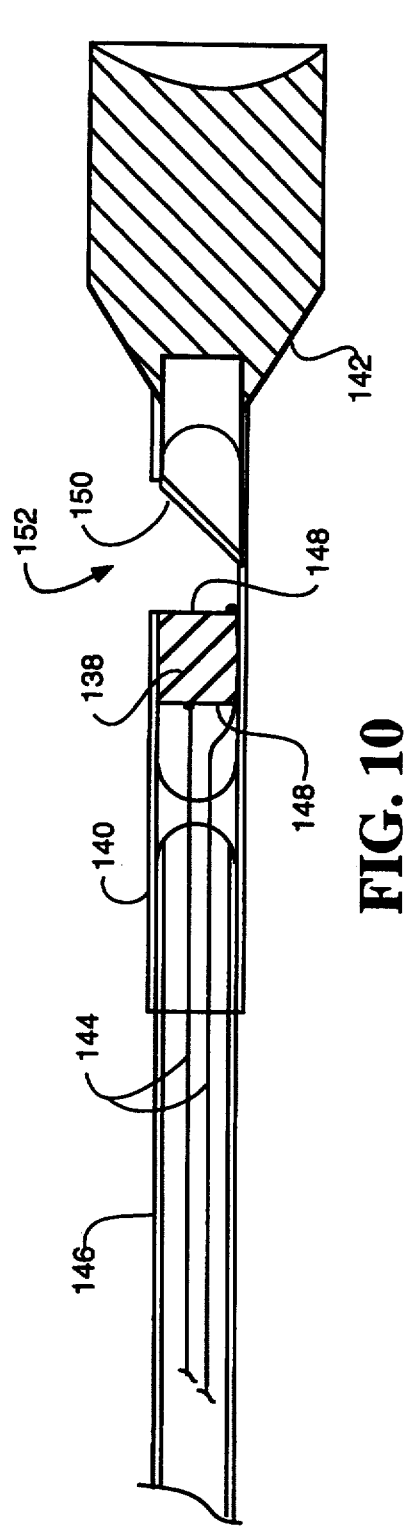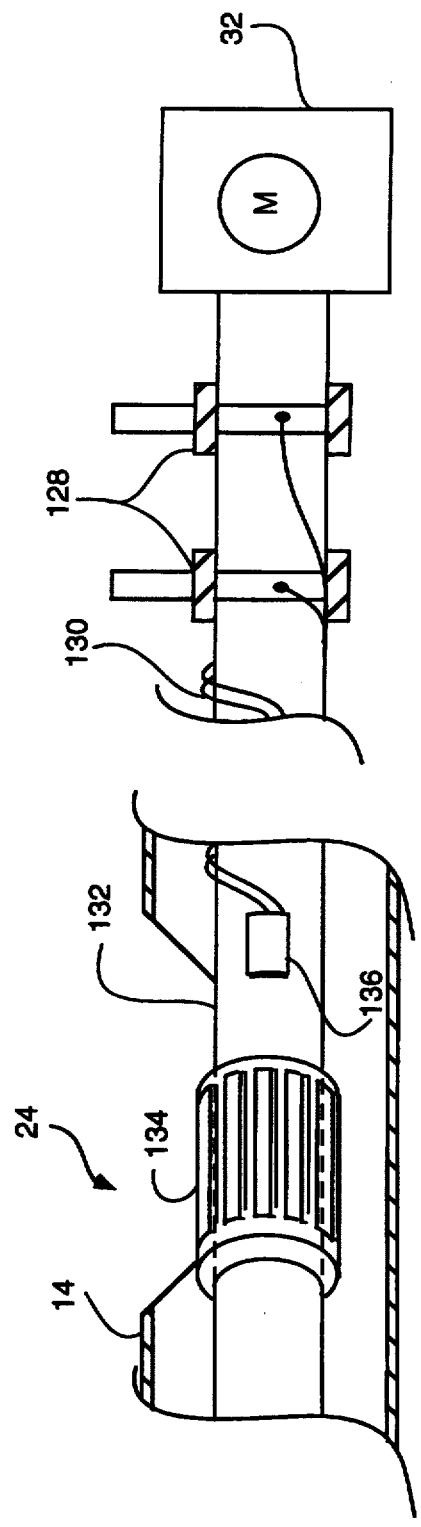
FIG. 10
FIG. 9

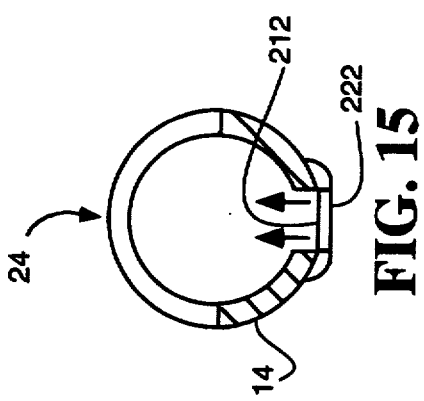
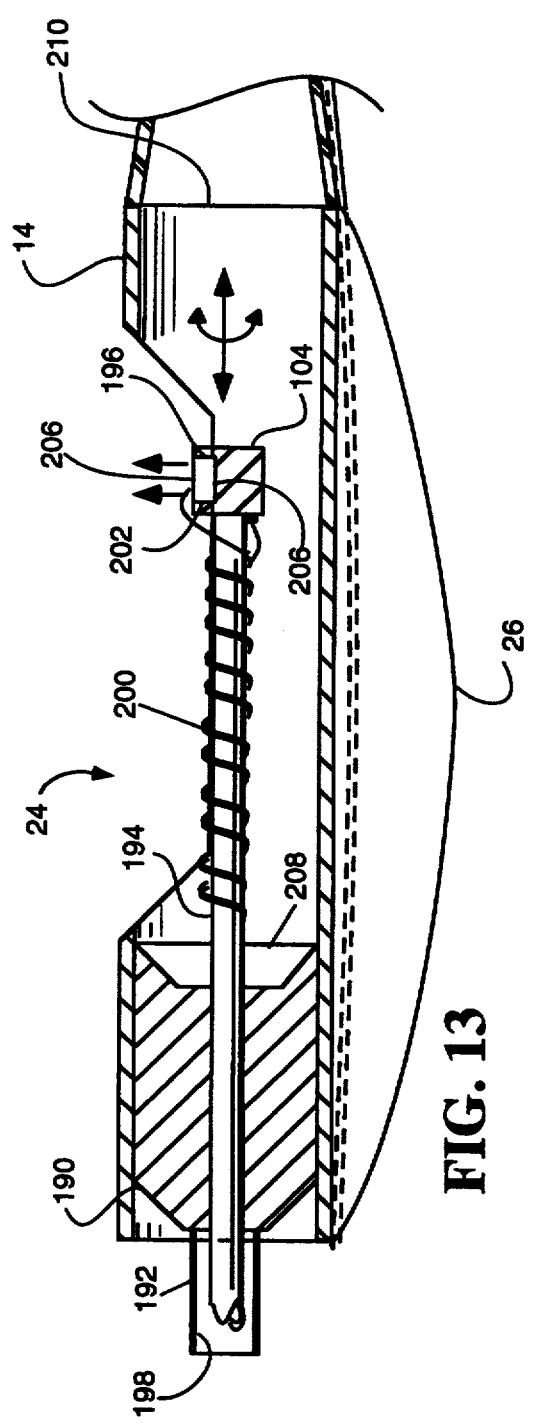
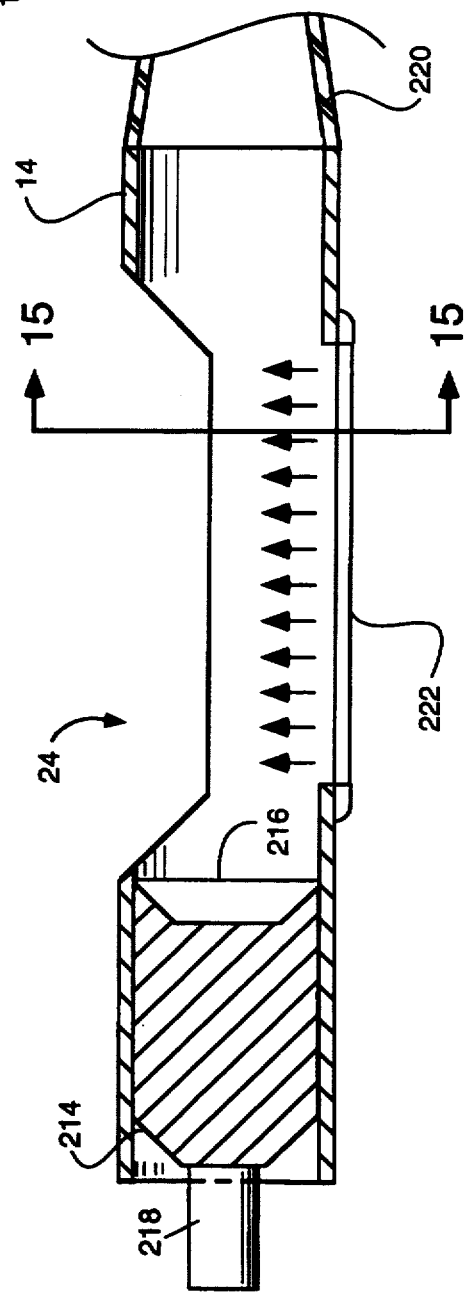

IMAGING ATHERECTOMY APPARATUS

RELATED APPLICATION

This application is a continuation-in-part of U.S. Ser. No. 08/051,521, filed Apr. 21, 1993, now abandoned.

BACKGROUND OF THE INVENTION

1. Field of the Invention

This invention relates to an ultrasonic imaging atherectomy apparatus for imaging and removing atherosclerotic plaque burden in human arterial and peripheral vasculature, and more particularly to improvements in imaging component form, connection, positioning and control for reducing cost, patient stress and the risk of induced emboli.

2. Previous Art

Atherosclerosis is a well known condition characterized by fatty and/or calcified deposits in the coronary arteries and peripheral blood vessels of the human body. These deposits are referred to generally as atheroma. There are many manifestations of atherosclerosis, including angina, hypertension, myocardial infarction, strokes, and the like.

Initially the atheroma deposit on the walls of blood vessels as soft, flexible accumulations. With time, the soft atherosclerotic material may become a calcified and hardened plaque. Stenoses generally refers to areas of blood vessel which are blocked by atheroma, plaque, or other material, the blocking material being referred to as plaque burden or stenotic material.

Several procedures have been developed for treating stenoses, such as balloon angioplasty where the stenoses are partially or completely compressed by a balloon catheter inserted into the blood vessel and inflated adjacent to a stenosis whereby the blood vessel becomes more open. An example of such a procedure and its apparatus is provided in Mueller et al, U.S. Pat. No. 5,041,089. Mueller teaches a catheter including a tubular structure having inner and outer walls. The outer wall is enlarged at a distal end of the catheter to define an annular lumen used to inflate the wall as a balloon. In this way the stenoses is compressed. However, this procedure is susceptible to re-occlusion of the vessel at a later time because the stenotic material is not removed.

A number of atherectomy procedures have been developed using various catheter instruments for surgically removing portions of the stenosis. Examples of such procedures are provided in U.S. Pat. Nos. to Gifford et al., No. Re. 33,569, Gifford, No. 5,071,425, and Simpson et al., No. 5,092,873, each of which is incorporated herein by reference. These patents generally disclose a housing having a window, a cutter enclosed within the housing and exposed through the window for removing a portion of the stenosis, a balloon used for urging the cutter against the stenotic material to be removed, a lumen for inflating and deflating the balloon, a housing and a flexible elongated catheter body connecting the housing and body.

Experience has shown such procedures to be valuable despite a necessity for repeated insertion and removal of different instruments as these are found to be better or worse suited for the situation arising during treatment. The repeated cycles of insertion and removal result in prolonged treatment time with an attendant cost and heightened risk of injury to the patient due to ischemia or damage to blood vessel walls.

Ultrasonic imaging has been used to improve identification of the nature, extent and location of the stenoses during surgery. Ultrasonic imaging has also been used to determine the method of treatment and the resultant effect. The use of such imaging has successfully reduced both treatment time and patient risk. Examples of the technique are presented in Yock, U.S. Pat. Nos. 5,000,185 and 4,794,931. As taught in these patents, ultrasonic energy is generated by a transducer located at a distal end of, or within a vascular catheter. The transducer is manipulated to sweep an ultrasonic signal in a desired pattern. Ultrasonic energy reflected from the interior surface of the blood vessel, including any stenosis or occlusion present, is processed and the result used to display an image or profile of the interior of the vessel.

The difficulties of design, manufacture and use of ultrasonic devices for ultrasonic imaging have been numerous. The size of material, typically less than 1 mm outside diameter and high frequency, typically greater than 20 Mhz, have made the selection of the materials quite important. In general, PZT ceramic is preferred because it converts energy, mechanical and electrical, more efficiently than other materials. However, PZT ceramic material lends itself to a phenomenon commonly referred to as "ringing" when not constructed to precise standards. Ringing is defined as the energy emitted by the transducer after the cessation of the transmitting signal. As will be appreciated, if the ringing continues it will mask the echo from near by tissue making the device unusable. PVDF films have also been used and while they do not typically exhibit ringing, such materials are not efficient at converting electrical energy to mechanical energy. However, such materials are efficient at converting mechanical energy to electrical energy. Additionally, such materials have high electrical output impedance making such materials unsuitable for driving a transmission lines directly.

In catheters which contain guiding means, the guide means take the form of cylindrical members, or flexible wires interior to the catheter. Both these structures, being generally centrally located in the catheter, increase the overall cross-section of the catheter, thus limiting its use in smaller blood vessels.

In those devices which combine the cutting and imaging functions in a single device, the physical proximity of the transducer and the cutting edge can result in unintended and unavoidable removal of healthy tissue as the combined transducer/cutter is manipulated during the scanning phase. The risk of induced emboli is thus increased.

What is needed is an improvement in transducer configurations which will allow better imaging capability at smaller catheter dimensions.

There is need also for a flexible guide means which will reduce the overall cross-section of catheters thereby allowing their use in smaller blood vessels.

Finally, there is a need for isolating the movement of the cutting edge from exposure to the area being analyzed during the process of moving or directing the ultrasonic energy for image scanning.

SUMMARY OF THE INVENTION

In general, it is an object of the invention to provide a catheter apparatus, for intravascular ultrasonography and atherectomy which separates the image scanning process from the cutting edge of the cutter moving inside the window of the housing.

Another object of the invention is to provide an apparatus of the above character which reduces the risk of inducing emboli while imaging.

A further object of the invention is to provide a guide means which improves the guiding capability of the catheter.

A further object of the invention is to provide improved signal-to-noise ratio of the ultrasonic images.

A further object of the invention is to reduce the effects of unwanted image artifacts generated by the ultrasonic transducer.

A further object of the invention is to reduce the effects of unwanted image artifacts caused by non-circularity in the cross-section of the elongate members of the catheter.

In accordance with the above objects and those that will be mentioned and will become apparent below, the atherectomy catheter for imaging and removing tissue from a stenotic site in a biological vessel comprises:

a catheter tube having proximal and distal ends, the catheter tube including a lumen;

a housing defining an elongated tube having proximal and distal ends and a longitudinal axis extending from one end to the other, the proximal end being connected to the distal end of the catheter tube, the housing including a longitudinal window, the window defining a window region;

cutting means for removal of tissue, the cutting means having proximal and distal ends and being adapted for rotational and axial manipulation within the window region;

transducer means for receiving an electrical input signal, for converting the input signal to ultrasonic energy, for radiating the ultrasonic energy, for receiving reflected ultrasonic energy, and for converting the received energy into an electrical output signal, the transducer means being adapted for directing the radiated energy rotationally and axially within the window region;

maneuvering means for manipulating the cutting means and for manipulating the transducer means to direct the radiated energy, the maneuvering means extending through the catheter tube lumen and including electrical coupling means for connecting the transducer means to a signal processing means;

signal processing means for receiving and for converting the transducer means output signal for being displayed as a three dimensional image; and display means for receiving the converted output of the signal processing means and for displaying the three dimensional image, whereby the atherectomy catheter may be inserted into a biological vessel, the transducer means then manipulated to perform an ultrasound scan of the vessel walls, the results being displayed as a three dimensional image to enable a precision removal of diseased tissue.

In a preferred embodiment, the maneuvering means includes separate transducer and cutter maneuvering members permitting independent control of these operative elements and reducing the chances of accidental injury during catheter positioning and during the imaging operations.

Alternative embodiments offer useful variations in transducer type, operative element maneuvering, electrical connection between transducer and the signal processing means, and arrangement of the guide wire lumen.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 3 is a partial side view of the housing portion of FIG. 1 showing an embodiment using independent maneuvering means and single acoustic transducer.

FIG. 4 is a partial side view of the housing portion of FIG. 1 showing an embodiment using independent maneuvering means and linear array.

FIG. 5 is a partial side view of an alternative using a spindle mounted transducer and independent maneuvering means.

FIG. 6 is a cross-sectional view through line 6—6 of FIG. 5.

FIG. 7 is a partial side view of the housing portion of FIG. 1 showing an embodiment using a linear array and a shared maneuvering member.

FIG. 8 is a is a partial side view of an alternative having the transducer mounted in a recess of the cutting means and using a reflective acoustic surface.

FIG. 9 is a partial side view of an alternative using a shared maneuvering member and an annular linear array.

FIG. 10 is a partial side view of an alternative using a shared maneuvering member including the transducer and an acoustic reflective surface.

FIG. 11 is a partial side view of an alternative having a shared maneuvering member and restricted transducer movement.

FIG. 12 is a cross-sectional view taken at line 12—12 of FIG. 11.

FIG. 13 is a partial side view of an alternative having the transducer distal the cutter.

FIG. 14 is a partial side view of an alternative having a housing mounted linear array.

FIG. 15 is a cross-sectional view taken at line 15—15 of FIG. 14.

FIGS. 16–18 are cross-sectional views of alternative electrical coupling on a torque tube.

DETAILED DESCRIPTION OF THE INVENTION

GENERAL OVERVIEW

Apparatus

Figure 1:
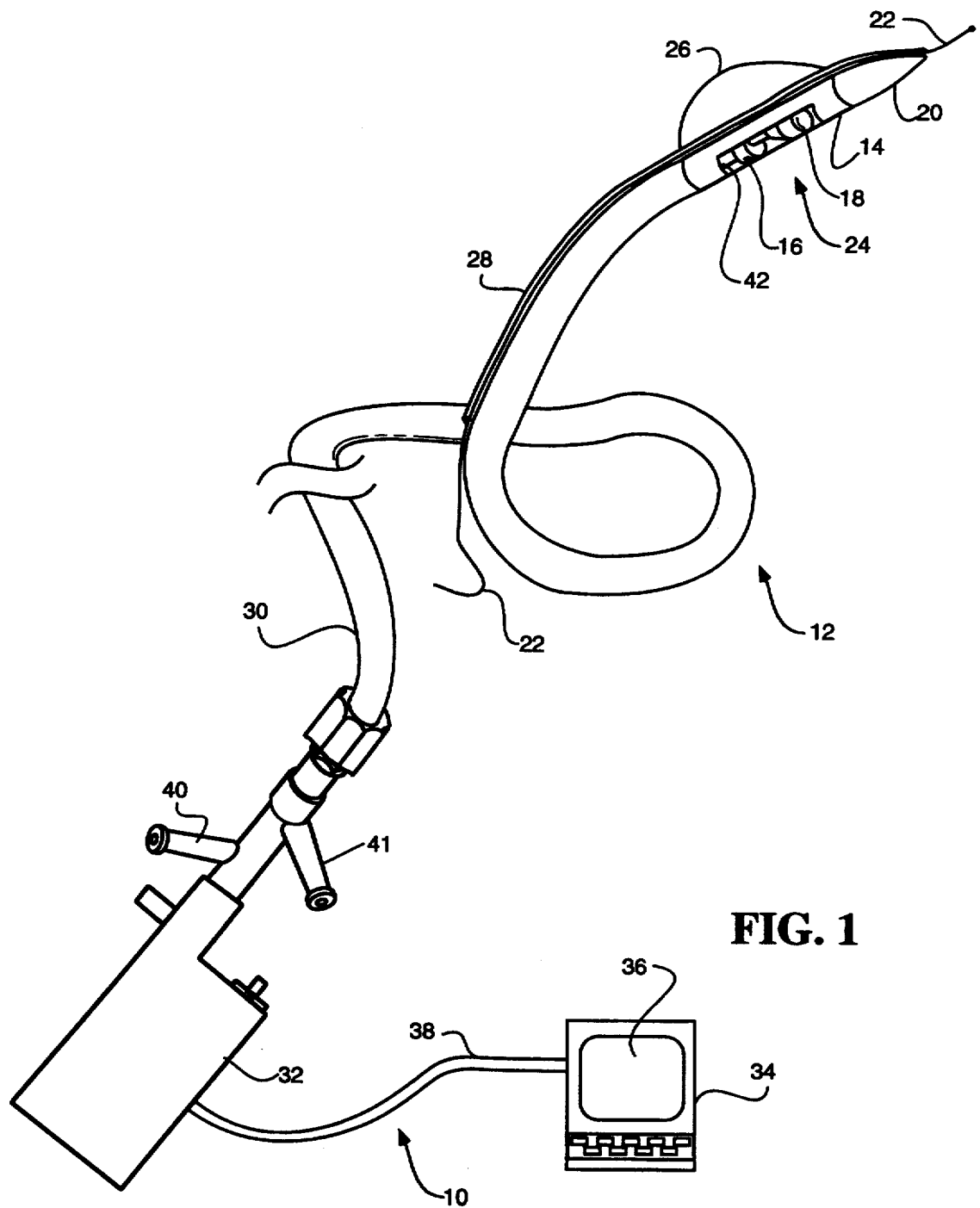
FIG. 1 is a general view of an imaging atherectomy apparatus in accordance with this invention.

The invention will now be described with respect to FIG. 1, which illustrates generally the imaging atherectomy apparatus 10. The instrument includes a catheter assembly 12 having a distal portion 14 for housing an ultrasonic imaging transducer 16 and a plaque burden cutter 18. Housing 14 is fitted at its distal end with a flexible nosecone 20 from which one end of a guidewire 22 extends distally. An opening 24 along one side of housing 14 provides access between the cutter 18 and stenotic tissue which is to be surgically removed from the walls of a biological vessel.

An inflatable balloon 26 is disposed along one side of the housing 14 opposite the opening 24. The balloon 26 may be inflated to urge the opening 24 against the tissue which is to be surgically removed. A guidewire lumen 28 is shown along one side of catheter assembly 12. The catheter assembly 12 is extended at its proximal end as a flexible cable assembly 30 for attachment to a motor drive unit 32 and signal processing and display units 34, 36.

The ultrasonic imaging transducer 16 and the plaque burden cutter 18 are independently manipulable via flexible mechanical connection through the flexible cable assembly 30. Electrical connection between the transducer 16 and the signal processing and display units 34, 36 are completed through flexible cable assembly 30 and instrumentation cable 38. There are two Infusion ports 40 and 41 located at the motor control unit permit a transfer of fluids via cable assembly 30 between the ports 40 and the catheter assembly 12. Infusion port 40 is the port for the contrast injection lumen and infusion port 41 is the port for the balloon inflation lumen.

The cutter 18 and the transducer 16 are connected to other, flexible maneuvering members 42 which are disposed within the tubular members 12, 14, and 30. In the motor drive unit 32, rotary and reciprocal motion are provided for the flexible drive members 42 by manual or motor operation. The motors are controlled by the signal processing unit 34. Three dimensional image information is generated from the signals received from the transducer 16 by circuitry in the signal processing unit 34 and is presented on a display 36.

Figure 2:
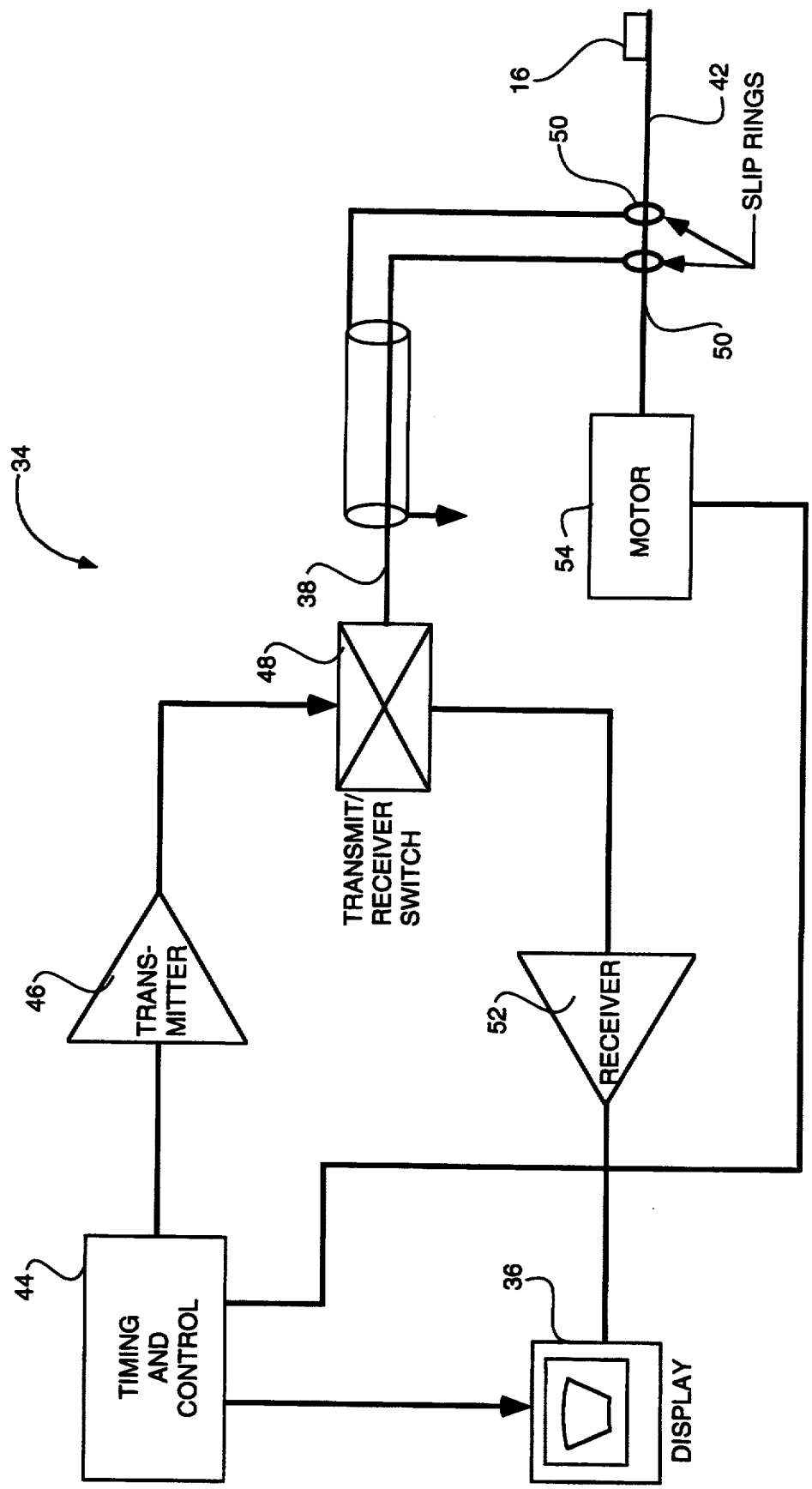
FIG. 2 is a schematic diagram of the signal processing unit in of FIG. 1.

FIG. 2 is a schematic diagram showing generally details of the signal processing unit 34 including the display unit 36. Overall control resides with timing and control circuitry 44 which typically involves use of a programmed general purpose computer. An output signal of the timing and control circuitry 44 is coupled to the acoustic transducer 16 via transmitter 46, transmit/receive switch 48, instrumentation cable 38, slip rings 50, and an electrical coupling which is typically made a part of the flexible maneuvering members 42.

Application of the output signal to the acoustic transducer 16 results in a radiation of acoustic energy by the transducer 16. Energy reflected from vessel walls and stenotic tissue is received by the transducer 16 which converts the received energy into an electrical signal. This transducer output signal is returned through transmit/receive switch 48 to receiver 52. The returned signal is processed and the result applied to the display unit 36 for a three dimensional display of the interior of the vessel walls and occluding plaque formations. One or more motors 54 are controlled by the timing and control circuitry 44 for maneuvering the transducer 16 and cutter 18 (not shown) via flexible maneuvering members 42.

Typical Operation

During operation, the catheter assembly 12 is inserted into a biological vessel and is positioned, typically with fluoroscopic aid, to a region known or believed to be occluded by plaque burden. Ultrasonic scanning proceeds by manual or electrically directed positioning of the catheter assembly housing window 24 and the ultrasonic transducer 16, which is typically independently movable within housing 14. Ultimately, the housing opening 24 is positioned adjacent to a stenotic site. The balloon 26 is then inflated to urge the housing 14 and its window 24 against a selected target plaque burden. The cutter 18 is then employed to remove that portion of the diseased tissue which is exposed through the opening 24.

A PREFERRED EMBODIMENT

Independent Maneuvering of Transducer and Cutter

With reference to FIG. 3, the apparatus of a preferred embodiment of the present invention is shown which permits the independent maneuvering of both the transducer 16 and the cutter 18. The flexible cable assembly 30 (FIG. 1) includes a central lumen (not shown) through which the maneuvering members 42 extend into the housing 14. The housing 14 includes the longitudinal window opening 24 through which access to plaque burden is made. The maneuvering members 42 include a hollow transducer torque tube 56 and a cutter torque cable 58. The cutter torque cable 58 extends through a lumen 60 of the hollow torque tube 56 into a window region of the housing 14 beyond the distal end of the torque tube 56. A proximal end of the housing 14 is connected to extend the distal end of the flexible cable assembly 30 (FIG. 1). The cutter 18 is connected to the distal end of the cutter torque cable 58, and the acoustic transducer 16 is mounted on an outer surface 62 of the distal end of the torque tube 56. Electrical coupling between the transducer 16 and the slip rings 50 (FIG. 2) is completed through helical conductors 64.

The proximal ends of the maneuvering members 42 extend through flexible cable assembly 30 to the motor control unit 32. Each of the maneuvering members, the torque tube 56 and the coaxial torque cable 58, are independently maneuverable, allowing the cutter 18 to be positioned distal the window 24 region of the housing 14 during acoustic imaging.

The elongate tubular assembly 12 (FIG. 1) includes a flexible catheter body which is similar in construction to a wide variety of vascular catheters which are well known in the art.

The flexible catheter body will usually comprise a very flexible tube formed by extrusion of an organic polymer, typically a thermoplastic, such as nylon, polyurethane, polyvinyl chloride (PVC), polyethylene, or the like. The tubes so formed may be reinforced or un-reinforced, with reinforcement being provided by metal wires, metal braided cables, or the like. The catheter body will typically have a length in the range from about 60 to 150 cm and a diameter in the range from about 3 to 11 French. For use in coronary applications, the catheter body will typically have a length from about 120 to 110 cm. The flexible catheter body combined with the metal reinforcement comprises a housing torque cable 30 (FIG. 1) for transferring rotational and translational movement, applied at the motor control unit 32 (FIG. 1) at the proximal end of the housing torque cable, to the housing assembly mounted at the distal end of the housing torque cable.

The housing torque cable 30 is connected to the proximal end of the housing 14 in a manner described in Gifford, U.S. Pat. No. 5,071,425. General considerations relating to the design and construction of atherectomy catheters are described in U.S. Pat. Nos. 4,979,951 and 5,092,873 and Re. 33,569 which are herein incorporated by reference.

The housing 14 is an elongate body of generally cylindrical shape. The housing 14 will usually have a length in the range from about 5 to 40 mm, more usually being in the range from about 15 to 25 mm. The housing 14 may be open, having one or more apertures, gaps, or the like, which allow for unrestricted passage of materials and acoustic energy between the interior of the housing and the external environment surrounding the housing as described in Gifford U.S. Pat. No. 5,071,425, hereby incorporated by reference.

The outer surface of the housing torque cable 30 is composed of or coated with a material to reduce friction such as urethane, as disclosed in Simpson U.S. Pat. No. 4,979,951 (hereby incorporated by reference), so the catheter assembly 12 (FIG. 1) can easily enter and slide within a biological vessel.

The window 24 is oriented along the longitudinal axis of the housing 14. The window 24 is an opening in the housing 14 which is formed by a suitable angular sector generally less than a half circle of the circumference of the housing 14 and extends axially for a suitable distance.

The transducer torque tube 56, typically formed of multi-stranded stainless steel wire, such as described by Simpson et al. U.S. Pat. No. 5,092,873 and incorporated by reference. The torque tube 56 is slidably and rotatably disposed inside a central lumen (not shown) of the flexible housing torque cable assembly 30.

The proximal ends of the transducer torque tube 56, the cutter torque cable 58 and the flexible housing torque cable 30 are connected to the motor drive unit 32 by conventional means such as described in Simpson, U.S. Pat. No. 4,771,774, hereby incorporated by reference.

Infusion ports 40 are connected to a balloon lumen (not shown) and are interposed as shown in FIG. 1 of U.S. Pat. No. 4,771,774 for introducing fluid to the balloon lumen to inflate and deflate the balloon 26 (FIG. 1) or to introduce other drugs and/or fluids such as radio-opaque fluids.

The distal end of the cutter torque cable 58 is solidly connected to the proximal end of the cutter 18 by conventional means such as solder or epoxy. The distal end of the transducer torque tube 56 terminates proximally to the point where the cutter torque cable 58 connects to the cutter 18. The acoustic transducer 16 is mounted on the outer surface 62 of the transducer torque tube 56. The acoustic transducer 16 is adjacent the distal end of the transducer torque tube 56 and is aligned to emit and receive ultrasonic energy radially to the axis of the tube 56. Electrical connection is made to the acoustic transducer 16 by an electrical coupling such as a pair of bifilar wires 64. The wires 64 are wound helically around the transducer torque tube 56.

The helical winding of the bifilar connection wires 64 provides a better approximation to a continuously smooth concentrically cylindrical surface than the alternative straight, parallel wires conventionally used. This reduces the non-uniformity of motion during rotation and improves the appearance of displayed three dimensional images.

The cutter 18 and the interior of the housing 14 are formed of circular cross-section and fit closely. The cutter 18 is adapted to move slidably and rotatably within the housing 14. The cutter 18 includes a circular cutting edge 66 which lies in a plane generally perpendicular to the longitudinal axis of the housing 14 and the cutter 18. The circular cutting edge 66 faces the distal direction of the housing 14, and is initially positioned into a recess 68 in the housing 14 distal to the window 24 while the housing 14 is being initially positioned within a biological vessel, and during scanning.

With reference to FIG. 2, the timing and control circuitry 44 generates output pulses which are used to drive the acoustic transducer 16. These pulses are nominally of 1 nano-seconds duration and represent a burst of RF energy generally in a range of 10–50 Mhz, having a typical frequency of 30 Mhz, plus or minus 10 percent. The output pulses generally have an amplitude in a range of 10–100 V peak to peak, typically at a value of 40 V peak to peak. The bursts of RF energy are repeated at intervals ranging from 20–32 times per second, typically at 30 times per second.

The acoustic transducer 16 of this embodiment of the invention is a single crystal formed of a suitable material such as quartz, lithium niobate, lithium tantalate and zinc oxide or of one of the piezoelectric ceramics such as lead titanate zirconate, barium titanate, or the thin films of PVDF.

Electrical connection between the bifilar wires 64 and the acoustic transducer 16 are made at regions 70 which are formed of gold foil or of films deposited by conventional means such as plating, evaporation, or sputtering. Regions 70 are connected to the bifilar wires 64 by conventional means such as solder.

Under excitation of signals as described above, the piezoelectric acoustic transducer 16 emits ultrasonic energy which is radiated outward through the window 24. Some of the energy emitted is reflected back from the tissue and stenotic plaque framed by the window 24 to the acoustic transducer 16 which now acts as an energy receiver. The acoustic transducer 16 then generates electrical output signals which correspond to the energy received. These transducer output signals are returned to the signal processing unit 34 where they are processed and the results presented to the display unit 35 for a three dimensional display of the interior of the vessel walls and occluding tissue.

Typical Operation

With respect to FIG. 1, the use and operation of the apparatus to remove an atheroma in the blood vessel of a patient is described below. An opening is prepared in a suitable vessel as, for example, the femoral artery, and the guidewire 22 is inserted. The guidewire 22 is positioned to a desired location in the vasculature while being observed, for example by fluoroscopic means (not shown). The catheter assembly 12 is then introduced and moved along the guidewire 22 until the housing 14 is adjacent to the atheroma to be removed. The housing 14 is rotationally positioned either manually or by the motor drive unit 32 and longitudinally positioned by manipulation until the window 24 is adjacent to the atheroma.

The atheroma is acoustically scanned by maneuvering the transducer 16 within the window region of the housing 14. This maneuvering is accomplished with the motor control unit 32 under manual or automatic sequencing. The motor control unit 32 maneuvers the proximal end of the transducer torque tube 56 resulting in corresponding axial and rotational movement of the transducer 16 within the window region. In this manner, that portion of the biological vessel walls and stenotic tissue accessible through the window 24 can be imaged and reproduced at the display unit 36.

The range of movement is usually restricted to lengths of about 5 to 20 mm at a rate of 0 to about 1 mm per second, and a reciprocating angular range of 0 to about 180 degrees at a rate of 0 to about 60 cycles per second. The preferred angle of reciprocation of this invention is about 120 degrees. The preferred reciprocation rate of this invention is about 30 cycles per second.

Alternatively, the transducer torque tube 56 may be manually translated by the clinician to produce the range of scanning motion resulting in the displayed image. The motor drive unit 32 has controls (not shown) for advancing and retracting the maneuvering members 42 (FIG. 1). These manual controls are substantially as shown in Simpson, U.S. Pat. No. 4,771,774, previously referenced. The results of the preferred translation are processed by the signal processing unit 34 and are resolved into two simultaneous displays.

A first display corresponds to that portion of a vessel wall and interior which are intersected by a plane perpendicular to the longitudinal axis of the housing 14 and directed radially and outwardly through the window 24. This display is presented to the viewer as a sector scan and represents an approximate 120° radial view through the window 24. The longitudinal displacement of this first plane within the window region of the housing 14 is fixed but can be manipulated by the controls of the signal processing unit 34. This manipulation is independent of the transducer translation and is achieved solely by means of signal processing. In this manner, the first displayed image appears to the viewer as a slice made through the vessel at a right angle to the housing axis.

A second display, made simultaneously with the first display in order to achieve the equivalent of a three dimensional presentation, corresponds to that portion of the vessel wall and vessel interior intersected by a second plane parallel to the housing axis and directed radially and outwardly through the window 24. This second display is in the familiar B-Scan (longitudinal scan) format. This second plane can be manipulated radially using the signal processing unit 34 and is independent of the manipulation of the first plane, as described above. The second image appears to the viewer as a longitudinal slice through the vessel radially parallel to the housing axis. This B-Scan image provides a side view of the portion of the vessel walls and vessel interior framed by the window 24.

During the time scanning is taking place, the housing 14 is repositioned by the flexible housing torque cable 30 to examine other regions to be imaged beyond that available at one fixed position of the window 24. During the movement of the transducer torque cable 56 for imaging, the cutter 18 stays in the recess 68. This precaution prevents the cutting edge 66 from being inadvertently exposed within the open window 24 and thereby minimizes the risk of creating emboli during scanning.

Scanning is repeated in this manner as desired. After the scanning operation is complete, the housing 14 is repositioned by the flexible housing torque cable 30 to the location chosen for removal of the atheroma identified during scanning.

Typically, before tissue removal is begun, the balloon 26 is inflated to force the window 24 into contact around the atheroma to be removed.

The cutter 18 is then withdrawn from the recess 68 and the motor drive unit 32 energized. The cutter 18 is advanced and rotated to engage and thereby remove the portion of the atheroma disposed within the window 24. The portion so removed will be driven forward by the cutter 18 and deposited in the recess 68.

The balloon 22 is then deflated. The catheter assembly 12 including housing 14 is free to be repositioned in the vessel for further scanning and removal operations or withdrawn entirely.

Once withdrawn, the recess 68 is cleaned of the material deposited and the apparatus reintroduced into the vessel, if required, for additional scanning or removal operations.

AN ALTERNATIVE EMBODIMENT

Linear Transducer Array

An alternate embodiment of the apparatus in accordance with this invention is shown in FIG. 4. A linear acoustic transducer array 72 is mounted on the transducer torque tube 74 by conventional means such as medical grade epoxy. The array 72 is adapted to produce and to receive a sequence of ultrasonic beam pulses perpendicular to and along the longitudinal axis of the array 72 when excited by control and power pulses connected to the array 72. The acoustic pulses are propagated perpendicular to the longitudinal axis and reflect from the tissue lying in a plane parallel to the longitudinal axis of the array 72. The length of the path scanned in the longitudinal direction will be that of the array 72. The array 72 is mounted by conventional means, such as medical grade epoxy, cyano acrylate adhesive or other adhesive so that the axis of scan is parallel to the axis of the transducer tube 74 and housing 14. The advantage of using a linear array 72 instead of a single transducer are that a longitudinal scan or B-scan can be produced without moving the transducer.

The separate transducer torque tube 74 and cutter torque cable 76 allow the motions of the scanning operation and cutting operation to be independent of each other. This feature retains the advantage of minimizing the risk of emboli creation during scanning.

The array 72 is connected (not shown) to integrated circuits 78 for multiplexing the electrical signals which drive the transducer array 72. The integrated circuits 78 are mounted adjacent to the array 72 by conventional means such as medical grade epoxy as described above.

The signal processing unit 34 is adapted to generate electrical signals to the integrated circuits 78 which multiplex the signals to cause the array 72 to emit an ultrasonic beam which sweeps through a suitable length in a plane perpendicular to the array 72. Scanning in this manner allows a display of images along the longitudinal axis of the transducer 72 without moving the transducer 72 or the cutter 18.

AN ALTERNATIVE EMBODIMENT

Spindle Mounted Transducer

With particular reference to FIGS. 5 and 6, there is shown another embodiment of the imaging atherectomy apparatus in accordance with the present invention. The housing 14 includes a single transducer 80 mounted in a recess 82 provided on a separate spindle 84. The recess 82 is adapted to receive the transducer 80. The spindle 84 is a torus shaped, electrically conductive body of rectangular cross-section having distal and proximal surfaces perpendicular to the spindle 84 axis. The spindle 84 also includes inner and outer surfaces parallel to the axis of spindle 84. The spindle 84 is formed of suitable material such as stainless steel. The inner surface diameter of the spindle 84 is adapted to enclose the cutter torque cable 86 and to match the diameter of the transducer torque tube 88 lumen and provide a communicating lumen therethrough. The recess 82 is on the outer circumference of the spindle 84. The transducer 80 is attached by conventional means such as conductive epoxy or other conductive adhesive in the recess 82.

This conductive attachment forms one side of the electrical contact to one of the conductive sides of the transducer 80. The spindle 84 proximal surface is mounted to the distal end of the transducer torque tube 88 by suitable means such as medical grade epoxy. Wire connections 90 for conducting signals between the transducer 80 and the signal processing unit 34 are made to the other conductive region 92 on the transducer 80 and to the spindle 84 and thus to the other conductive region 92 of the transducer 80.

Cutter 94 is connected to a distal end of cutter torque cable 86. The cutter 94 includes a circular cutting edge 96 for removal of plaque burden. Housing recess 98 is provided as describe above for storage of the cutting edge during housing maneuvering and scanning, and for temporary storage of removed tissue.

FIG. 6 is a cross-sectional view through the apparatus of FIG. 5 at line 6—6. Outer housing 14 is shown enclosing within a central lumen the transducer torque tube 88. The cutter torque cable 86 is shown enclosed within a lumen of the torque tube 88.

FIG. 6 is used also to show a cross-sectional view of a balloon lumen 102, and a guidewire lumen 104 and guidewire 106. These additional features of FIG. 6 are not part of FIG. 5. The balloon lumen 102 is connected to balloon 26 of FIG. 1 and is used to inflate and deflate the balloon 26 via infusion ports 40. The guidewire lumen 104 of FIG. 6 corresponds to the guidewire lumen 28 of FIG. 1, while the guidewire 106 of FIG. 6 corresponds to the guidewire 22 of FIG. 1.

AN ALTERNATIVE EMBODIMENT

Shared Maneuvering Member

Referring to FIG. 7, another embodiment of the imaging atherectomy apparatus in accordance with this invention is shown. Many of the elements shown in FIG. 7 are similar to those described above for FIGS. 1 and 4, and are therefore numbered accordingly.

The embodiment includes a cutter torque cable 100, a cutter 18, a linear transducer array 72, a housing 14, a flexible housing torque tube 30 (see FIG. 1), a window 24, multiplexing integrated circuits 78 and connecting wires 64.

The proximal end of housing 14 is mounted on the distal end of the housing torque tube 30 (not shown). The window 24 provides an opening aligned longitudinally, as before. The proximal end of the cutter 18 is mounted to the distal end of the cutter torque cable 100.

In this embodiment, the linear transducer array 72 is mounted on the cutter torque cable 100 adjacent to the joining of the cutter 18 and the distal end of the cutter torque cable 100. The array 72 is oriented as before with the scanning plane parallel to the axis of the cutter torque cable 100 and facing radially outwardly through the window 24. The linear transducer array 72 is connected as before to the integrated circuits 78.

The integrated circuits 78 are connected to the signal processing unit 34 as before by bifilar wires 64 wound helically around the cutter torque cable 100. The acoustic transducer array driving signals are supplied by the signal processing unit 34 to the integrated circuits 78. These driving signals are conditioned as described above to sweep the ultrasonic beam emitted by the array 72 in a longitudinal direction without the necessity of moving either the transducer array 72 or the cutter 18.

This structure provides the capability of performing scanning operations while allowing the cutter 18 to remain in the housing recess 68 as before described, thereby minimizing the risk of creating emboli during scanning.

AN ALTERNATIVE EMBODIMENT

Transducer in Recess of Cutter

Still another embodiment of the imaging atherectomy apparatus in accordance with this invention is shown in FIG. 8. This embodiment includes as before a housing 14 having a window 24, a cutter 108 having a body of cylindrical shape, having distal and proximal ends, slidably disposed in the housing 14, and a cutter torque cable 110.

The cutter 108 proximal end is mounted to the distal end of the cutter torque cable 110. The proximal ends of the flexible housing torque cable 30 (FIG. 1 ) and the cutter torque cable 110 are connected as before to the motor drive unit 32.

A cutter body recess 112 is provided on the outer surface of the cutter body 108 for receiving the transducer 114. The cutter body 108 defines a first surface 116 of the recess 112 transverse to the cutter 108 axis and located at the proximal end of the body recess. Fist surface 116 is adapted to receive the transducer 114. Transducer 114 is thus oriented to emit ultrasonic energy parallel to the axis of the cutter 108 and emitting in a distal direction.

The transducer 114 is mounted with conductive epoxy in the recess 112 as described above.

The cutter body 108 also defines a second surface 118 of the recess 112 located distal the first surface 116. The second surface 118 is adapted to receive an acoustic reflective surface 120. The second surface 118 of the cutter body recess 112 and the acoustic reflective surface 120 are oriented to be in a plane transverse and at an acute angle from the perpendicular to the body 108 axis, generally of a sufficient angle to deflect the beam, for example 45°, whereby the perpendicular is directed radially outward and through the window 24.

The mounting method for the transducer 114 and reflective surface 120 are as generally described above.

Connection wires 122 for signals to and from the transducer 114 are connected as before to the transducer conductive regions 124. One of the wires 122 connects from the body of the cutter 108 which is in conductive contact with one conductive region 124. The other wire 122 connects to the other conductive region 124 of the transducer 114.

Scanning for this embodiment is performed by moving the entire housing 14 while the transducer 114 is exposed at the distal end of the window 24 and the cutter 108 is positioned in the housing recess 68 at the distal end of the housing 14, whereby the circular cutting edge 126 is shielded from the window 24 opening. Scanning can also be performed while the cutter 108 is translated forward and passes along the window 24 in a distal direction or while the cutter 108 is translated in a proximal direction past the window 24. Images are generated and displayed from the transducer output signals which are returned to the signal processing unit 34.

AN ALTERNATIVE EMBODIMENT

Circular Transducer Array

With respect to FIG. 9 another embodiment of the imaging atherectomy apparatus in accordance with this invention is shown. This embodiment includes a housing 14 having a window 24, a motor drive unit 32, a slip ring, brush and contact assembly 128, connecting wires 130, and a single torque tube 132 shared by both a cutter (not shown) and a transducer array 134.

The torque tube 132 is connected proximally to the motor drive unit 32 as described above.

Array 134 is a circular array of acoustic emitters divided into a number of equally spaced segments ranging in number from four to 360. The preferred number of emitters is 64. The array is adapted to project and receive acoustic beams in a radial direction outwardly from the torque tube axis. The array 134 is mounted on a portion of the torque tube 134 proximally adjacent to the cutter head (not shown). The array 134 is connected to an integrated circuit 136 by conventional means such as gold wire bonds (not shown), as previously described.

Integrated circuit 136 is adapted for multiplexing and for controlling the power and RF signals between the transducer array 134 and the signal processing unit (not shown). The integrated circuit 136 is mounted on the torque tube 132 adjacent to the array 134 by conventional means such as epoxy.

Electrical connections between the integrated circuit 136 and the signal processing unit are made through the connecting wires 130 and the slip ring, brush and contact assembly 128.

Power and RF pulses from the signal processing unit are adapted to generate acoustic beam pulses from sequential segments of the array 134 whereby the beam reciprocates repetitively through an angle adapted to include the opening of the window 24. The rate of reciprocation is from 0 to 60 cycles per second, preferably 30 cycles per second.

The acoustic energy reflected from tissue or plaque burden exposed within housing window 24 is received by the array 134 and is transformed into electrical signals which are de-multiplexed by the integrated circuit 136 and are subsequently processed and displayed as described above.

AN ALTERNATIVE EMBODIMENT

Shared Maneuvering Member

With regard to FIG. 10 an alternate embodiment of the imaging atherectomy apparatus in accordance with this invention is shown. This embodiment includes a single transducer 138 mounted inside a hypotube 140, a cutter 142, wire connections 144, and a cutter torque tube 146.

The hypotube 140 has distal and proximal ends and an axis extending through the hypotube from one end to the other. The axis of the hypotube 140 is aligned with the axis of the cutter torque tube 146. The distal end of hypotube 140 is connected to the proximal end of the cutter 142. The proximal end of the hypotube 140 is connected to the distal end of the cutter torque tube 146.

The transducer 138 is mounted inside the hypotube 140 by means such as an insulating epoxy or similar adhesive, and is oriented to emit acoustic energy parallel to the axis of the hypotube 140 and in a direction distal of the hypotube 140.

Electrical bonding between the connecting wires 144 and conductive regions 148 of the transducer 138 are accomplished using solder or conductive adhesive as previously described. One of the connecting wires 144 contacts the conductive region 148 at the proximal end of the transducer 138. The proximal conductive region 148 of the transducer 138 is adapted to be insulated from the electrically conductive hypotube 140.

The distal conductive region 148 of the transducer 138 is adapted to be connected to the hypotube 140 by a means such as conductive epoxy. The other one of the connecting wires 144 is connected to the hypotube 140 by conventional means such as described above.

Connecting wires 144 continue proximally through the hypotube 140 and through the cutter torque tube 146 to a slip ring, brush and electrical contact assembly (not shown) as previously described.

An acoustic reflective surface or mirror 150 is mounted within the hypotube 140 adjacent to an opening 152 in the hypotube 140 outer circumference. The acoustic reflective surface 150 is mounted perpendicularly to a line at essentially 45 degrees from the axis of the hypotube 140. This line passes through the center of the hypotube opening 152. The acoustic beam emitted from the transducer 138 is thereby directed perpendicularly to the axis of hypotube 140, and then outwardly through the opening 152.

The opening 152 is formed by removing a suitable portion of the outer surface of the hypotube 140. The opening 152 is adapted to pass the acoustic beam from the transducer 138 and to receive acoustic energy which has been reflected from the external environment.

The transducer 138 and the acoustic reflective surface 150 are spaced apart by a suitable distance ranging from 0.5 to 1.5 mm which reduces or eliminates the effect of the undesirable artifacts created by the "ring down" effect of PZT transducers previously described. This enhances the ability of capturing acoustic images closer to the axis of hypotube 140 since the artifacts occur in a region of no interest, i.e. within the hypotube 140. The use of an acoustic reflective surface 150 of a convex shape provides a degree of acoustical focusing which operates to enhance a signal to noise ratio and, under appropriate conditions, to improve the three dimensional imaging capability of the invention.

AN ALTERNATIVE EMBODIMENT

Restricted Transducer Maneuvering

With respect to FIG. 11, there is shown a side view of an alternative embodiment employing a shared maneuvering member and having restricted transducer movement. The distal end of the housing 14 is provided with a generally conical, flexible member 154 having a pointed distal end 156. This flexible member is generally referred to as a nosecone.

A flexible, slidably movable guide member Or wire 158 is provided which passes through the external rail guidewire lumen 24. The guidewire 158 is made of a suitable metal such as stainless steel, having a diameter in the range of 0.010 to 0.014 inches.

The guidewire lumen 24 is made of a suitable flexible material such as polyamide or teflon ®, having an inner diameter in the range of 0.016 to 0.018 inches and a wall thickness about 0.001 inches.

The nosecone 154 has a lumen portion 160 on the external surface. This lumen potion is aligned to and communicates with the guidewire lumen 24, whereby the guidewire 158 can be carried by the housing 14 and the catheter assembly 12 (FIG. 1) for aiding steering of the housing 14 into the desired vasculature.

The rail guidewire lumen 24 extends from the distal end of the nosecone 154 along the housing 14, and along the flexible housing torque cable 30 (FIG. 1) to a point near the motor drive unit 32 (FIG. 1).

The balloon 26, which is used for urging the housing 14 against the atheroma to be removed, is affixed to the housing 14 at a region directly opposite the housing window 24 by one of a number of methods. For example, see Gifford et al, U.S. Pat. No. 5,071,425 previously referenced. A balloon lumen (not shown) communicates with the balloon 22 whereby a fluid may be introduced and withdrawn to inflate and deflate the balloon 26. The proximal end of the balloon lumen communicates with a commercially available fluid manifold (not shown) of suitable type for introducing a fluid.

In this embodiment, the transducer 162 is mounted on a spindle 164. The spindle 164 is a torus shaped body of rectangular cross-section. The spindle 164 has distal and proximal ends, both perpendicular to the torus axis. The spindle 164 further has inner and outer circumferential surfaces parallel to the spindle axis.

A spindle recess 166 adapted to receive the transducer 162 is provided on the outer surface of the spindle 164. The recess is facing outwardly in the direction of the housing window 24. The transducer 162 is mounted in the spindle recess 166. The recess 166 and the transducer 162 are adapted to face perpendicularly to the axis of the spindle 162 and directed toward essentially the center of the window 24 opening.

The transducer 164 is attached to the spindle by suitable means such as conductive epoxy.

The spindle 164 is provided with a pair of flanges 168 mounted on the outer circumferential surface of the spindle 164, generally transverse to the transducer 162 and spindle 164 axes. The flanges 168 protrude from the spindle 164 outer surface in a direction radial to the spindle 164 axis.

The flanges 168 are adapted to slide in a pair of slots 170 provided on opposite sides of the housing 14. The slots 170 are oriented in the longitudinal direction of the housing 14, and are adapted to receive the flanges 168.

A rotatable thrust bearing 172 is adapted to mount between the inner circumferential surface of the spindle 164 and the outer circumference of the cutter torque tube 174. The thrust bearing 172 is adapted to allow the cutter torque tube 174 and the cutter 176 to rotate independently of the spindle 164 and transducer 162. The thrust bearing 172, flanges 168 and the slots 170 cooperate so that the spindle 164 and the transducer 162 remain angularly stationary with respect to the housing 14 as the cutter 176 turns. The thrust bearing 172 additionally is adapted to provide rigid longitudinal coupling between the cutter torque tube 174 and the spindle 164 so that the spindle 164 and the cutter 176 move longitudinally together. The thrust bearing 172 is mounted to the external surface of the cutter torque tube 174 and to the internal surface of the spindle 164 by suitable means such as epoxy.

Electrical connection between the signal processing unit 34 (FIG. 1) and the transducer 162 is formed by wire connections 178. Electrical connection between the wires 178 and the transducer 162 is made to conductive regions 180 on the transducer 162. One of the wires 178 connects to the top surface of the transducer 162 by conductive epoxy or solder. The other one of the wires 178 connects to the conductive spindle 164 with conductive epoxy or solder. The spindle 164 is contacted to the transducer 162 with conductive epoxy.

The connection wires 178 include a fixed section 182 and a flexible section 184. The fixed section 182 is configured and connected to the signal processing unit 34 (FIG. 1) as previously described. The fixed section 182 remains stationary with respect to the housing 14.

The flexible section 184 is adapted to allow the transducer 162 to move longitudinally with the cutter 176 as the cutter torque tube 174 and the cutter 176 move in a longitudinal direction with respect to the housing 14. The flexible section 184 of the wire connections 178 is one of a member selected from the group of conductive flexible members such as conductive coil springs, conductive bellows, and conductive accordion springs. These conductive members are made from beryllium copper (97.9% Cu-1.9%Be-0.2%Ni or Co) alloy or the like.

The cutter torque tube 174 and wire connections 178 to the motor drive unit 32 (FIG. 1) and to the signal processing unit 34 (also FIG. 1) are as previously described.

Once the housing 14 is positioned, image scanning is performed while the cutter 176 and the transducer 162 are translated longitudinally to form a B-scan image. Scanning will start with the cutter 176 and its circular cutting edge 186 positioned in the housing recess 188 so that the circular cutting edge 186 is shielded from the tissue outside the window 24. Scanning proceeds as the spindle 164 and the transducer 162 are moved proximally along the longitudinal axis of the housing 14.

The advantage of mounting the transducer 162 on the spindle 164 as described above is that it provides a predetermined relationship between the region of plaque burden scanned by the transducer 162 and the region which will be cut by the cutter 176.

This predetermined relationship ensures that once the housing 14 is aligned with the plaque burden to be removed, that the cutter 176 will be aligned with the maximum extension of the portion of the plaque burden protruding through the window 24.

FIG. 12 is a cross-sectional view taken through the spindle 164 at line 12—12 of FIG. 11. Numerals used to identify elements shown in FIG. 12 are identical to those used for the same elements and features shown in FIG. 11. The flanges 168 are shown fitting slidably within the housing slots 170 on two sides of the spindle 164. The spindle mounted transducer 162 is located to emit and receive acoustic energy through the housing window 24. The cutter torque tube 174 is shown fitted to the inner circumference of the toroidal spindle 164. The balloon 26 is attached to the housing opposite the window 24, and the guidewire lumen 28 provides a conduit for the guidewire 158.

AN ALTERNATIVE EMBODIMENT

A Distal Transducer

With particular regard to FIG. 13, there is shown another embodiment of the imaging atherectomy apparatus in accordance with this invention. The housing 14 includes a cutter 190, a cutter torque tube 192, a transducer torque cable 194, a transducer 196 and a window 24. The housing 14 is connected to a flexible housing torque tube (not shown) as described before. The cutter torque tube 192 is provided with a lumen 198 therethrough. The lumen 198 is adapted to slidably and rotatably enclose the separate transducer torque cable 194 and the wire connections 200 to the transducer 196. The transducer 196 is mounted in a barrel recess 202 by means previously described.

The barrel recess 202 is formed on the outer circumferential surface of a circular barrel 204 having proximal and distal ends and an axis coaxial with the transducer torque cable 194 axis. The circular barrel 204 proximal end is mounted to the distal end of the transducer torque cable 194, and is disposed distally to the cutter 190. Wire connections 200 to the transducer 196 conductive regions 206 are as described above.

In the scanning process, the cutter 190 is positioned proximally to the proximal end of the window 24 while the transducer 196 is translated along the axis of the housing 14. This sequence keeps the circular cutting edge 208 isolated from the window 24 opening to reduce the risk of emboli formation. The scanning and image formation process is performed as previously described.

The transducer 196 and the cutter 190 may be moved independently during scanning or cutting operations as desired by the clinician.

A housing recess 210 is provided distally of the distal end of the window 24 opening for receiving the removed plaque as the cutter 190 is moved past the distal end of the window 24.

AN ALTERNATIVE EMBODIMENT

Housing Mounted Transducer Array

Another embodiment of the imaging atherectomy apparatus in accordance with this invention is shown in FIG. 14. This embodiment includes a housing 14 having a housing window 24 and an array window 212, a cutter 214 having a circular cutting edge 216, a cutter torque cable 218, a nosecone 220, a multiplexing integrated circuit (not shown), wire connections (not shown) from the signal processing unit 34 (FIG. 1) to the integrated circuit, a linear transducer array 222, and connection means (not shown) as previously described from the integrated circuit to the linear transducer array 222.

The cutter 214 is disposed within the housing 14. The cutter 214 connection to the cutter torque cable 218, and the housing 14 connection to the flexible housing torque tube (not shown) are as previously described.

In this embodiment, the transducer takes the form of a linear array 222. The linear array 222 is adapted to be mounted at the edges of the array 222 in the array window 212 by suitable means, such as adhesive. The location of the array window 212 on the housing 14 is adapted so as to be diametrically opposite the housing window 24. The array window 212 is adapted to receive the linear array 222 mounted so that the emitting surface of the array 222 faces the housing window 24, whereby the array 222 scans the region defined by the opening of the housing window 24 in the manner previously described.

Longitudinal or B-scanning operations are performed under control of the signal processing unit 34 (FIG. 1) by sweeping the acoustic beam along the plane parallel to the housing 14 axis passing through the housing window 24 and linear array 222 while the cutter 214 and circular cutting edge 216 are positioned proximally to the proximal end of the housing window 24.

The housing 14 is positioned rotationally and longitudinally by the flexible housing torque tube 30 (FIG. 1) in the blood vessel as desired. Scanning can be done before, during and after the cutter 214 is advanced for cutting stenoses.

FIG. 15 is a cross-sectional view taken at line 15—15 of FIG. 14. The housing 14 includes the array window 212 which is located opposite the housing window 24. The liner transducer array 222 is mounted within the array window 212 and directs its acoustic energy outwardly through the housing window 24.

ELECTRICAL COUPLING ALTERNATIVE EMBODIMENTS

FIG. 16

FIG. 16 is a cross-sectional view taken through a torque tube 224 of typical construction as previously described. Electrical conductors 226 are shown disposed within a flexible liner 228 of the torque tube 224. The electrical conductors 226 are generally 28 to 44 AWG and the liner 228 of flexible insulator such as teflon ®, being of about 0.001 inch wall thickness. As shown in FIG. 3, the electrical conductors 226 are generally disposed in a helical manner within the flexible liner 228. The helical winding pitch of the conductors 226 generally takes the range of 3 to 10 turns per inch, having a preferred value of approximately 5 turns per inch.

The advantage of the helical winding is that it more nearly approximates uniform concentricity than two straight conductors along the longitudinal axis. This reduces the tendency of a non-uniformly circular body to introduce angular rotational asymmetry due to varying forces on the protrusion of the conductors 226 in a radial direction as the torque tube 224 rotates. This rotational asymmetry can result in imaging artifacts which distort the displayed image.

FIG. 17

With respect to FIG. 17, an alternate embodiment of the helical connection wires of the imaging atherectomy apparatus in accordance with this invention are shown in cross-section. This embodiment includes fiat, braided wires 230 of thickness generally between 0.0005 inch to 0.002 inch, and having a preferred value of 0.001 inch. The braided wires 230 range in width from 0.050 inch to 0.200 inch, and have a preferred width of 0.100 inch.

These flat braided wires 230 are helically wound around the torque tube 232, and are covered and held in place by a heat shrink covering 234.

FIG. 18

With respect to FIG. 18 an alternate embodiment of the connection wires of the imaging atherectomy apparatus in accordance with this invention are shown in cross-section. This embodiment includes a torque tube 236, and a pair of conducting elongate thin semi-circular shells 238 disposed within a flexible liner 240.

The advantage of the thin conducting shells 238 is that they do not have to be wound helically around the torque tube 236 to inherently provide a more uniform cross-section than helical wound round or flat wires.

Rail PLATFORM ALTERNATIVE EMBODIMENTS

FIG. 19

Figure 19:
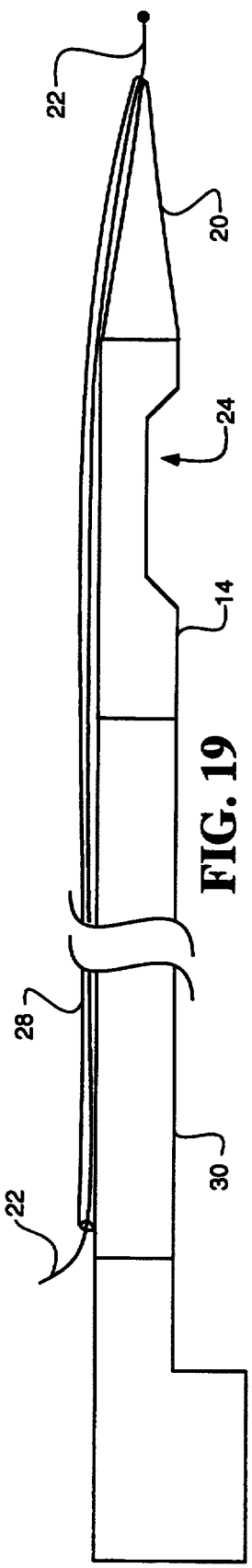
FIGS. 19–22 are plan views of alternative rail guide wire configurations.

FIG. 19 is a side view of an embodiment of the atherectomy catheter in accordance with the present invention. The catheter includes a flexible housing torque tube 30, a housing 14 having a window opening 24, a nosecone 20, and a Rail guidewire lumen 28 disposed along the catheter from a point near the proximal end of the housing torque tube 30 and extending along the housing 14 and the nosecone 20 to a point near the distal end of the nose cone. The Rail guidewire 22 is enclosed within the guidewire lumen 28.

FIG. 20

Figure 20:
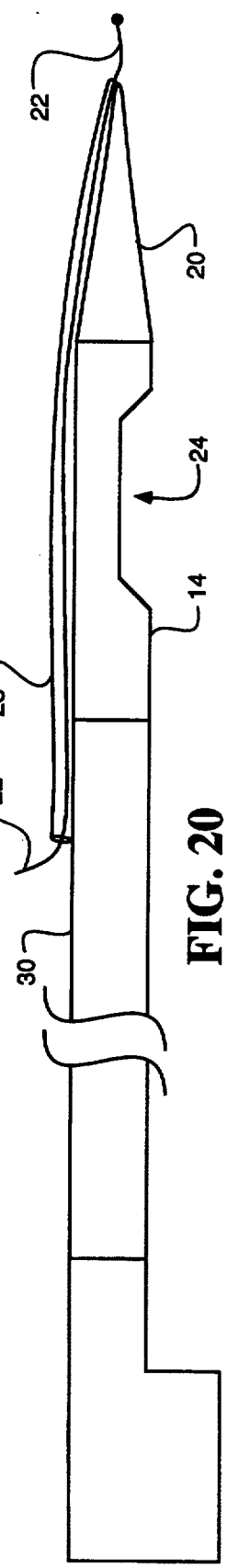

With respect to FIG. 20, another embodiment of the Rail guidewire 22 of the imaging atherectomy apparatus in accordance with this invention is shown. The Rail guidewire lumen 28 is terminated anywhere along the flexible housing torque tube 30 proximal to the housing 14 thereby allowing the entire catheter assembly 12 (FIG. 1) to be removed from the patient for cleaning or other purposes, without removing the guidewire 22.

FIG. 21

Figure 21:
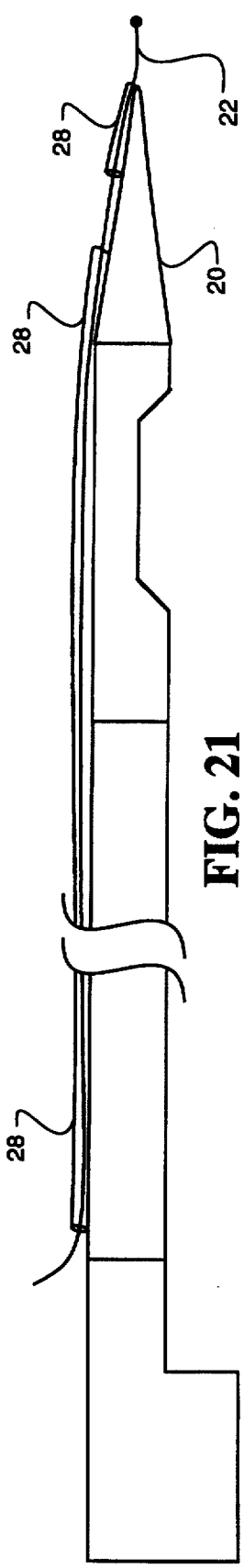

With respect to FIG. 21 another embodiment of the Rail guidewire 22 of the imaging atherectomy apparatus in accordance with this invention is shown. In this embodiment, much of the guidewire lumen 28 is removed along the nosecone 20 to permit greater flexibility of the nosecone 20 and thereby better device tracking through the vasculature.

The main body of the guidewire lumen 28 ends distally to the housing 14. A short segment, or portion of guidewire lumen 28 about 1 to 2 mm long remains near the distal end of the nosecone 20 thereby capturing and directing the Rail guidewire 22 while improving the flexibility of the nosecone 20.

FIG. 22

Figure 22:
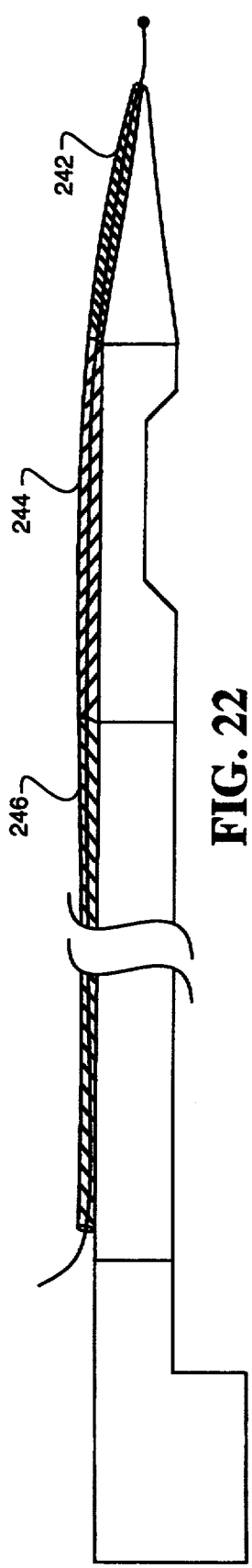

With respect to FIG. 22 another embodiment of the Rail guidewire 22 of the imaging atherectomy apparatus in accordance with this invention is shown. Previous embodiments have been described as a lumen depicted as a continuous length of a polymeric material.

The guidewire lumen of this embodiment of the invention is made up of multiple segments of different materials, specifically a distal segment 242, a middle segment 244, and a proximal segment 246. The proximal segment 246 is made of a flexible polymer, the middle segment 244 is made of a semi-rigid polymer or a metal, and the distal segment 242 is made of a very flexible polymer.

AN ALTERNATIVE EMBODIMENT

Integrated Transducer Package

Figure 23:
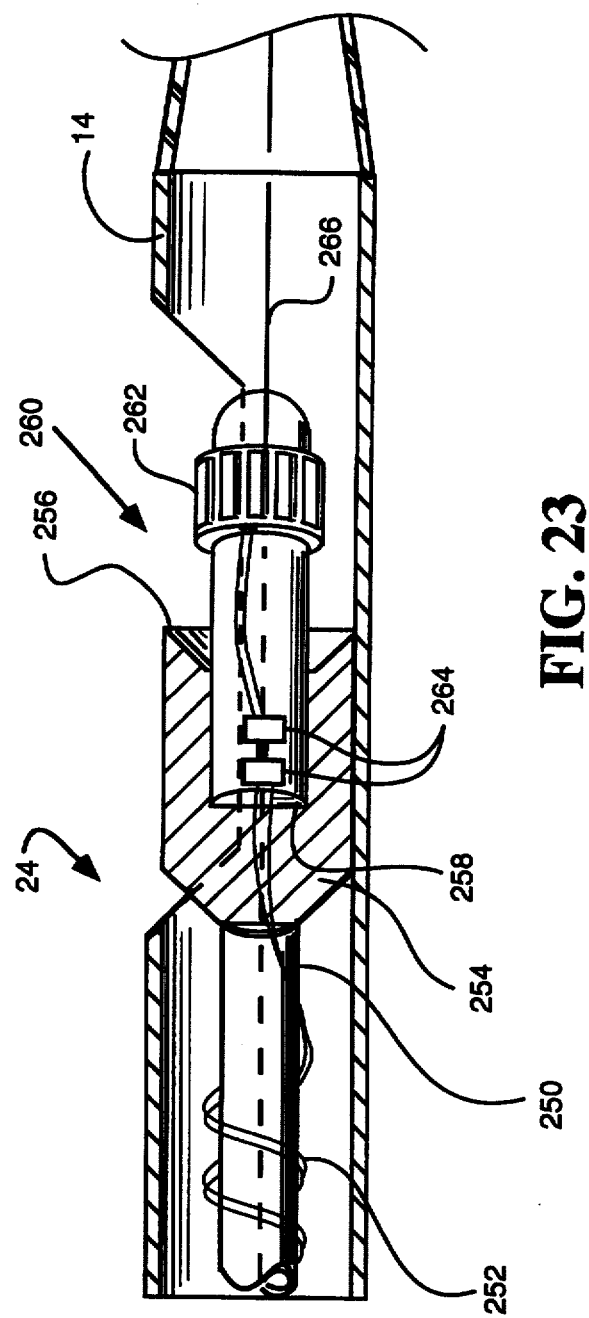
FIG. 23 is a partial side view of an embodiment having the transducer distal the cutter and sharing the same torque tube.

Another embodiment of the imaging atherectomy apparatus in accordance with this invention is shown in FIG. 23. The housing 14 includes a window 24 as described previously. A cutter torque cable 250 has a cutter 254 attached distally. The cutter 254 has a distal cutting edge 256 and an axial recess 258. An integrated package 260 is mounted within the axial recess 258 by means of an adhesive. The integrated package 260 has an elongated cylindrical shape and extends distally beyond the cutting edge 256. The integrated package 260 supports an annular linear transducer array 262 disposed on the surface of the integrated package 260. The annular array 262 is located a sufficient distance from the cutting edge 256 to avoid interference between the acoustic radiation and the cutting edge 256 during scanning. The integrated package 260 also includes integrated circuits 264 used for signal conditioning and for multiplexing. Electrical connection is made within the integrated package 260 between the annular array 262 and the integrated circuits 264. Electrical connection is also made between the integrated circuits 264 and the helical conductors 252 shown wound upon an outer surface of the torque cable 250. An opening from one end to the other of the integrated package 260 is provided for passage therethrough of a guidewire 266.

In use, the cutter torque cable is manipulated both in the longitudinal and in the axial directions to control movement of the cutting edge 256 and the annular transducer 262. During scanning the cutting edge 256 can be withdrawn proximally from the window region to prevent accidental cutting or damage to tissue.

While the foregoing detailed description has described several embodiments of the imaging atherectomy system in accordance with this invention, it is to be understood that the above description is illustrative only and not limiting of the disclosed invention. It will be appreciated that it would be possible to modify the transducer and cutter and the maneuvering means or connection wires to include or exclude various elements within the scope and spirit of this invention. Thus the invention is to be limited only by the claims as set forth below.

What is claimed is:

1. An atherectomy catheter for imaging and removing tissue from a stenotic site in a biological vessel, comprising:

a catheter tube having proximal and distal ends, the catheter tube including a lumen;

a housing defining an elongated tube having proximal and distal ends and a longitudinal axis extending from one end to the other, the proximal end being connected to the distal end of the catheter tube, the housing including a longitudinal window, the window defining a window region, the housing includes a first surface and a second surface, the second surface being an acoustic reflector;

cutting means for removal of tissue, the cutting means having proximal and distal ends and being adapted for rotational and axial manipulation within the window region;

transducer means mounted on the first surface for receiving an electrical input signal, for converting the input signal to ultrasonic energy, for radiating the ultrasonic energy against the second surface which reflects the acoustic energy, for receiving reflected ultrasonic energy, and for converting the received energy into an electrical output signal, the transducer means being adapted for directing the radiated energy rotationally and axially within the window region;

maneuvering means for manipulating the cutting means and for manipulating the transducer means to direct the radiated energy, the maneuvering means extending through the catheter tube lumen and including electrical coupling means for connecting the transducer means to a signal processing means;

signal processing means for receiving and for converting the transducer means output signal for being displayed as a three dimensional image; and display means for receiving the converted output of the signal processing means and for displaying the three dimensional image, whereby the atherectomy catheter may be inserted into a biological vessel, the transducer means then manipulated to perform an ultrasound scan of the vessel walls, the results being displayed as a three dimensional image to enable removal of diseased tissue.

2. The atherectomy catheter of claim 1 wherein the maneuvering means further comprises:

a torque tube, the torque tube includes the electrical coupling means, the torque tube having a proximal end, a distal end, an outer surface and a torque tube lumen extending from the proximal end to the distal end through the torque tube, the outer surface being adapted to fit slidably and rotatably within the catheter tube lumen;

a cutter torque cable adapted to fit slidably and rotatably within the torque tube lumen and extending beyond the distal end of the torque tube;

further wherein the transducer means is connected to the distal end of the torque tube, and the cutting means is connected to the distal end of the torque cable, whereby the transducer means and the cutting means can be independently manipulated in both axial and rotational position within the window region, and the cutting means can be moved distal the window region during scanning.

3. The atherectomy catheter of claim 2 wherein the transducer means further comprises a linear acoustic array connected to an integrated circuit means for multiplexing array signals for connection to the electrical coupling means, and further wherein the linear array emits and receives acoustic energy in a beam being directed in a plane parallel to the longitudinal axis of the housing, whereby the transducer torque tube can be manipulated to direct the beam radially through the window and the multiplexing means can be employed to direct the beam longitudinally within the plane.

4. The atherectomy catheter of claim 2 wherein the transducer means further comprises a toroidal member having an outer surface including a recess mounted acoustic transducer for emitting and receiving acoustic energy radially to the housing axis, a proximal end of the toroidal member being connected to the distal end of the transducer torque tube, the toroidal member being adapted for axial and rotational movement within the housing, the transducer being connected to the electrical coupling means.

5. The atherectomy catheter of claim 1 wherein the maneuvering means further comprises:

a cutter torque cable having an outer surface adapted to fit within the catheter tube lumen and having a distal end extending into the window region, the torque cable including the electrical coupling means;

further wherein the cutting means is connected to the distal end of the torque cable and the transducer means is connected to the torque cable near the proximal end of the cutting means, whereby the transducer means and the cutting means are simultaneously manipulated within the window region, and the cutting means can be moved distal the window region during scanning.

6. The atherectomy catheter of claim 5 wherein the transducer means and the cutting means are simultaneously manipulated in both an axial and a rotational position.

7. The atherectomy catheter of claim 6 wherein the transducer means is mounted longitudinally on the outer surface of the torque cable and further comprises a linear acoustic array connected to an integrated circuit means for multiplexing array signals for connection to the electrical coupling means, and wherein the linear array emits and receives acoustic energy in a beam being directed in a plane parallel to the longitudinal axis of the housing, whereby the cutter torque cable can be manipulated to direct the beam radially through the window and the multiplexing means can be employed to direct the beam longitudinally within the plane.

8. The atherectomy catheter of claim 6 wherein the cutting means further comprises an elongated body extending from near the proximal end to the distal end of the cutting means and having an outer circumference adapted to fit closely within the elongated tube defined by the housing, the body of the cutting means defining an axis extending from one end of the body to the other and being coaxial with the longitudinal axis of the housing, the body also having a recess on the outer circumference being oriented in the axial direction for receiving the transducer means, the first surface is in the recess near the proximal end of the body, the first surface being perpendicular to the body axis and being adapted for mounting the transducer means thereon, the second surface is in the recess being at a sufficient angle to deflect the beam from the body axis, the second surface being an acoustic reflector for reflecting acoustic energy emitted and received by the transducer means in a direction perpendicular to the body axis.

9. The atherectomy catheter of claim 8 wherein the angle equals 45°.

10. The atherectomy catheter of claim 8 wherein a length is defined from the first to the second surface, the length being adapted to introduce a time delay in a signal propagation from the transducer to the stenotic site such that extraneous signal artifacts introduced by the transducer are suppressed.

11. The atherectomy catheter of claim 8 wherein the second surface comprises a concave acoustic reflector adapted for focusing the emitted and the received acoustic energy.

12. The atherectomy catheter of claim 6 wherein the transducer means includes an annular transducer array disposed coaxially on the outer surface of the torque cable, the transducer means including the transducer array and integrated circuit means for multiplexing array signals for connection to the electrical coupling means, the annular transducer array having linear segments being arranged parallel to the housing longitudinal axis and selectable by the integrated circuit means for controlling an angular direction of transducer emitted and received acoustic energy in a plane parallel to the axis.

13. The atherectomy catheter of claim 6 wherein the cutter torque cable further comprises a flexible cutter torque tube having proximal and distal ends and a lumen extending from one end to the other, the distal end of the cutter torque tube being terminated by a proximal end of a hypotube, the hypotube having a distal end being connected to the proximal end of the cutting means, a medial region of the hypotube having a longitudinal opening, the transducer means being located inside the medial portion of the hypotube proximal the opening for emitting and receiving acoustic energy parallel to the longitudinal axis, the acoustically reflective second surface being located within the hypotube distal the transducer means, the reflective surface having an orientation at a sufficient angle to deflect the beam to the longitudinal axis for redirecting the acoustic energy in a plane parallel to the longitudinal axis.

14. The atherectomy catheter of claim 13, wherein the angle is 45°.

15. The atherectomy catheter of claim 5 wherein the transducer means further comprises:
- a toroidal spindle having an axis parallel to the longitudinal axis of the housing and having an inner surface being adapted for enclosing the cutter torque cable near the proximal end of the cutting means, the outer surface of the spindle being adapted for longitudinal movement within the housing;
- means connected to the torque cable and to the inner spindle surface for maintaining a fixed longitudinal separation between the spindle and the cutting means while permitting the torque cable to rotate freely within the spindle;
- at least one flange on the outer surface of the spindle extending in a direction radially to the spindle axis, the flanges slidably engaging longitudinal slots defined by the housing, the flanges and slots being disposed and cooperating to maintain a fixed spindle rotational orientation within the window region; and
- a transducer being located within a recess on the outer surface of the spindle for emitting and receiving acoustic energy through the longitudinal window.

16. The atherectomy catheter of claim 15 wherein there are a plurality of flanges.

17. The atherectomy catheter of claim 15, wherein the electrical coupling means includes stretchable conductive connection means for completing an electrical connection between the spindle mounted transducer and the signal processing means.

18. The atherectomy catheter of claim 15 wherein the stretchable connection means comprises elastic conductors.

19. The atherectomy catheter of claim 15 wherein the stretchable connection means comprises conductive accordion shaped springs.

20. The atherectomy catheter of claim 15 wherein the stretchable connection means comprises conductive bellows shaped springs.

21. The atherectomy catheter of claim 15 wherein the stretchable connection means comprises conductive coil springs.

22. The atherectomy catheter of claim 1 wherein the maneuvering means further comprises:
- a cutter torque tube having proximal and distal ends and a lumen extending from one end to the other through the tube, and having an outer surface adapted to fit slidably and rotatably within the catheter tube lumen;
- a transducer torque cable including the electrical coupling means and adapted to fit slidably and rotatably within the cutter torque tube lumen and extending beyond the distal end of the torque tube;

further wherein the transducer means includes a barrel having proximal and distal ends and defining an axis coaxial with the housing defined longitudinal axis, the proximal end of the barrel being connected to the distal end of the transducer torque cable, the barrel having an outer surface including a recess, an acoustic transducer being mounted within the recess for emitting and receiving acoustic energy radially to the longitudinal axis; and further wherein the cutting means is connected to the distal end of the cutter torque tube and includes a lumen extending from the cutting means proximal to distal ends for passage of the transducer torque cable therethrough, whereby the transducer means and the cutting means can be independently manipulated in both axial and rotational position within the window region, and the cutting means can be moved proximal the window region during scanning.

23. The atherectomy catheter of claim 1 wherein the maneuvering means further comprises a cutter torque cable having a distal end, the proximal end of the cutting means being connected to the distal end of the torque cable for axial and rotational manipulation of the cutting means within the window region, and wherein further, the housing includes an array window being open opposite the housing window and extending parallel to the housing longitudinal axis within the window region, the transducer means further comprising a linear acoustic array disposed within the array window for emitting and receiving acoustic energy through the housing window in a plane parallel to the longitudinal axis, and the catheter tube and housing including the electrical coupling means, whereby the cutting means can be positioned proximal the window region during scanning and the catheter tube and housing manipulated to adjust the direction and location of the acoustic energy.

24. The atherectomy catheter of claim 1 wherein the maneuvering means includes a cutter torque cable having an outer surface adapted to fit within the catheter tube lumen and having a distal end extending into the window region, the torque cable including the electrical coupling means;
- wherein the cutting means is connected to the distal end of the torque cable near the proximal end of the cutting means, the cutting means having an axial recess at its distal end; and
- wherein the transducer means comprises an integrated package, the package being mounted within the axial recess of the cutting means and extending distally the distal end of the cutting means, the integrated package including an annular transducer array distal to the cutting means and being connected to integrated circuit multiplexing means for multiplexing array signals for connection to the electrical coupling means, the annular transducer array having linear segments being arranged parallel to the housing longitudinal axis and selectable by the integrated circuit multiplexing means for controlling an angular direction of transducer emitted and received acoustic energy in a plane parallel to the axis, the transducer means being electrically connected to the electrical coupling means.

25. The atherectomy catheter of claim 24 further including a longitudinal opening extending through the integrated package for passage of a guidewire therethrough.

26. An apparatus adapted for connection to a catheter cable assembly having a cutter for cutting tissue and a transducer for emitting and receiving signals, for insertion into a patient's blood vessel for viewing and treating vascular stenosis, the apparatus comprising:
- a housing defining an elongated tube having an outer surface, a distal end, a proximal end and a longitudinal axis extending from one end to the other through the tube, the housing outer surface including a longitudinal window;
- cutting means for removal of tissue including a cutter and having distal and proximal ends and being adapted for positioning within the housing and adjacent to the window, the cutting means includes a first surface perpendicular to the longitudinal axis and a second surface, the second surface reflects ultrasonic energy;
- transducer means mounted on the first surface for radiating ultrasonic energy along the longitudinal axis to the second surface and for converting received reflected energy into an electrical output signal, the transducer means being adapted for electrical connection to a signal processing and display means for converting the output signal to a form suitable for display as a three dimensional image, the transducer means being further adapted for positioning within the housing and adjacent to the window; and
- maneuvering means for controlling the angular and axial position of the cutter means and the transducer means relative to the housing, the maneuvering means being located within a lumen of the catheter cable assembly,
- whereby the apparatus may be inserted into a patient's blood vessel, the transducer means may then be maneuvered in both an angular and an axial position to perform an ultrasound scan, and its output signal processed for display of the interior of the vessel enabling a precision removal of tissue.

27. An apparatus as set forth in claim 26, wherein the adaptation for electrical connection of the transducer means to the signal processing and display means includes a torque cable having proximal and distal ends, a lumen extending from one end to the other through the cable, and an inner surface being lined with a flexible material and including a pair of conducting elongate thin semi-circular shells disposed between the liner and the inner surface.

28. An apparatus as set forth in claim 26, wherein the adaptation for electrical connection of the transducer means to the signal processing and display means includes a torque cable having proximal and distal ends, a lumen extending from one end to the other through the cable, and an outer surface having a bifilar pair of electrical conductors wound in a helix around the torque cable, the electrical conductors being connected to the transducer means at a distal end and to the signal processing and display means at a proximal end.

29. An apparatus as set forth in claim 26, wherein the adaptation for electrical connection of the transducer means to the signal processing and display means includes a torque cable having proximal and distal ends, a lumen extending from one end to the other through the cable, and an outer surface having parallel transmission lines disposed thereon as a double helix, the double helix extending from one end of the torque cable to the other, and being electrically connected to the transducer means at a distal end and to the signal processing and display means at a proximal end, the double helix and torque cable being enclosed in a heat shrink tube.

30. An apparatus as set forth in claim 26, wherein the adaptation for electrical connection of the transducer means to the signal processing and display means includes a torque cable having proximal and distal ends, a lumen extending from one end to the other through the cable, and an inner surface being lined with a flexible material and including a pair of conducting elongate thin semi-circular shells disposed between the liner and the inner surface.

31. An imaging atherectomy catheter, comprising:
- a catheter tube including a lumen extending there through;
- a housing for enclosing a tissue cutter and an ultrasonic transducer, the housing defining an elongated tube being an extension of a distal end of the catheter tube and having an outer surface including a longitudinal window, the housing being adapted for rotational and longitudinal positioning of the cutter and the transducer within a region defined by the window, the cutter being formed with a first surface and a second surface, the second surface reflects ultrasonic energy and is angled with respect to the first surface, the ultrasonic transducer mounts on the first surface an radiates ultrasonic radiation toward the second surface; and
- positioning means connected for manipulation of the axial and longitudinal positions of the cutter: and the transducer, the positioning means extending through the catheter tube lumen and including means for electrical connection between the transducer and signal processing and display means for processing a transducer output signal and for presenting a processed result as a three dimensional image of an interior of a biological vessel,
- whereby the catheter can be inserted into the biological vessel and the window region positioned proximate a stenotic site for imaging stenotic tissue, the transducer position can then be manipulated to produce an output signal for display as the three dimensional image, and the cutter can then be manipulated to remove tissue.

32. The imaging atherectomy catheter of claim 31, wherein the housing includes a nosecone having a proximal end being connected for extending a distal end of and reducing a diameter of the housing for simplifying passage through the biological vessel, and wherein the imaging atherectomy catheter includes guide means for guiding the passage of the extended housing within the biological vessel, the guide means including a Rail platform connected externally to the catheter tube and the extended housing.

33. An imaging atherectomy catheter as set forth in claim 32, wherein the Rail platform includes a guidewire lumen extending from a location proximate the distal end of the catheter tube along the extended housing, the guidewire lumen slidably enclosing a flexible guidewire.

34. An imaging atherectomy catheter as set forth in claim 32, wherein the Rail platform includes a guidewire lumen having at least two segments, the segments being longitudinally separated along a portion of the nosecone, the guidewire lumen slidably enclosing a flexible guidewire.

35. An imaging atherectomy catheter as set forth in claim 32, wherein the Rail platform includes a guidewire lumen having at least three segments, a first segment being attached along a length of the catheter tube and extending to a proximal end of the housing, the first segment being made of a flexible material, a second segment being attached external to the housing, the second segment being of a material more flexible than the first segment, and a third segment being attached to the nosecone and being made of a material more flexible than the material of the second segment, the lumens of the three segments forming a single, continuous lumen and enclosing a flexible guidewire.

36. The imaging atherectomy catheter of claim 32 wherein the Rail platform includes a guidewire lumen extending along a substantial portion of the catheter tube and the extended housing, the guidewire lumen slidably enclosing a flexible guidewire.

* * * * *